(12) United States Patent
Lee et al.

(10) Patent No.: US 11,905,054 B2
(45) Date of Patent: Feb. 20, 2024

(54) PHASE CHANGE PRESSURE PACKING APPARATUS AND METHOD OF MANUFACTURE / USE THEREOF

(71) Applicants: W. Davis Lee, Rockport, ME (US); Warren R. Kirsch, Palo Alto, CA (US); Christian T. Metcalfe, Mercer Island, WA (US)

(72) Inventors: W. Davis Lee, Rockport, ME (US); Warren R. Kirsch, Palo Alto, CA (US); Christian T. Metcalfe, Mercer Island, WA (US)

(*) Notice: Subject to any disclaimer, the term of this patent is extended or adjusted under 35 U.S.C. 154(b) by 1 day.

(21) Appl. No.: 17/480,128

(22) Filed: Sep. 20, 2021

(65) Prior Publication Data

US 2022/0002015 A1 Jan. 6, 2022

Related U.S. Application Data

(63) Continuation-in-part of application No. 17/016,311, filed on Sep. 9, 2020, which is a continuation-in-part
(Continued)

(51) Int. Cl.
| | |
|---|---|
| *B65B 31/00* | (2006.01) |
| *B65B 25/00* | (2006.01) |
| *B65D 85/72* | (2006.01) |
| *A23C 13/12* | (2006.01) |
| *B65D 83/14* | (2006.01) |
| *A61L 9/03* | (2006.01) |
| *A23C 9/152* | (2006.01) |

(52) U.S. Cl.
CPC .......... *B65B 31/003* (2013.01); *A23C 9/1524* (2013.01); *A23C 13/12* (2013.01); *A61L 9/03* (2013.01); *B65B 25/005* (2013.01); *B65D 83/14* (2013.01); *B65D 85/72* (2013.01); *A61L 2209/134* (2013.01)

(58) Field of Classification Search
CPC ... B65B 31/002; B65B 25/005; A23C 9/1524; A23C 13/12; A61L 9/03; A61L 2209/134; B65D 83/14; B65D 85/72
See application file for complete search history.

(56) References Cited

U.S. PATENT DOCUMENTS

| | | | | |
|---|---|---|---|---|
| 3,763,900 A | * | 10/1973 | Solms-Baruth | ....... B65B 31/003 141/3 |
| 2022/0022695 A1 | * | 1/2022 | Lee | ....... B65B 25/005 |

* cited by examiner

*Primary Examiner* — Thomas M Wittenschlaeger
(74) *Attorney, Agent, or Firm* — Kevin H. Hazen; Hazen Patent Group, LLC

(57) ABSTRACT

The invention comprises a method for packaging a dispensable substance, such as a food product, whipped cream, a hydrocarbon, or an air freshener, the method comprising the steps of: placing a first product component into a container, the container comprising a valve dispensing port; adding a second product component into the container, the second product component comprising at least one of: (1) a solid form of the second product component and (2) a liquid form of the second product component; sealing the container; and warming, after the step of sealing, the second product component in the container at least ten degrees Celsius, where the step of warming results in a phase change of all of the second product component into a gas phase, at least a portion of the gas phase of the second product component dissolving into the first product component to form the dispensable substance.

17 Claims, 12 Drawing Sheets

Related U.S. Application Data of application No. 17/007,851, filed on Aug. 31, 2020, now abandoned, which is a continuation-in-part of application No. 17/002,767, filed on Aug. 25, 2020, now Pat. No. 11,534,030, which is a continuation-in-part of application No. 16/999,061, filed on Aug. 21, 2020, now Pat. No. 11,432,684, which is a continuation-in-part of application No. 15/125,434, filed as application No. PCT/US2016/050919 on Sep. 9, 2016, now abandoned.

(60) Provisional application No. 62/217,463, filed on Sep. 11, 2015.

PHASE CHANGE PRESSURE PACKING APPARATUS AND METHOD OF MANUFACTURE / USE THEREOF

CROSS REFERENCES TO RELATED APPLICATIONS

This application is a continuation-in-part of U.S. patent application Ser. No. 17/016,311 filed Sep. 9, 2020, which is a continuation-in-part of U.S. patent application Ser. No. 17/007,851 filed Aug. 31, 2020, which is a continuation-in-part of U.S. patent application Ser. No. 17/002,767 filed Aug. 25, 2020, which is a continuation-in-part of U.S. patent application Ser. No. 16/999,061 filed Aug. 21, 2020, which is a continuation-in-part of U.S. patent application Ser. No. 15/125,434 filed Sep. 12, 2016, which is a national stage application under 35 U.S.C. § 371 and claims priority to international application no. PCT/US2016/050919, filed Sep. 9, 2016, which claims the benefit of U.S. provisional patent application No. 62/217,463 filed Sep. 11, 2015; and
    is related to U.S. provisional patent application No. 61/953,160 filed Mar. 14, 2014 and U.S. provisional patent application No. 62/052,376 filed Sep. 18, 2014,
all of which are incorporated herein in their entirety by this reference thereto.

BACKGROUND OF THE INVENTION

Field of the Invention

The invention relates to a pressure packing apparatus and method of manufacture/use thereof.

Discussion of the Prior Art

Nitrous oxide, which is also known as dinitrogen monoxide, $N_2O$, and/or "laughing gas" and colloquially known as nitrous is classified by the United Nations Intergovernmental Panel on Climate Change as a potent greenhouse gas with a global warming potential over three hundred times that of carbon dioxide, $CO_2$. Nitrous oxide is the fourth most common greenhouse gas, behind water vapor, carbon dioxide, and methane.

Nitrous oxide is persistent in the atmosphere, with an average lifetime of one hundred twenty years, and reacts destructively with protective ozone in the stratosphere, which results in a reduction in ultraviolet light absorbance and a greater percentage of harmful incident ultraviolet light from the sun reaching the planet's surface. It follows that a reduction in the emission of nitrous oxide has significant positive long-term benefits to life and materials/structures on earth. Hence, compositions with a smaller percentage of nitrous oxide and/or methods used to reduce nitrous oxide emissions, such as in food preparation, are beneficial.

Nitrous oxide is commonly used to make whipped topping, such as a whipped cream. Whipped cream is used as an element of various food items, such as beverages, crepes, pancakes, and/or desserts. An estimated 500 million eight-gram nitrous oxide gas cartridges are used worldwide annually, resulting in the release of over four million metric tons of nitrous oxide, which has a global warming impact equivalent to 1.2 billion metric tons of carbon dioxide.

In addition, nitrous oxide, is a substance of abuse that is easy to obtain and difficult to detect. Huffing of nitrous oxide to achieve an analgesic, which is often referred to as a narcotic high, has become an abuse problem.

What is needed is a container pressurized with two or more chemicals, method of manufacture thereof, and/or a method of use thereof.

SUMMARY OF THE INVENTION

The invention comprises a pressure packing apparatus and method of manufacture or use thereof.

BRIEF DESCRIPTION OF THE DRAWINGS

A more complete understanding of the present invention is derived by referring to the detailed description and described embodiments when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that are performed concurrently or in a different order are illustrated in the figures to help improve understanding of embodiments of the present invention.

DETAILED DESCRIPTION OF EXEMPLARY EMBODIMENTS

The invention comprises a method for packaging a dispensable substance, such as a food product, whipped cream, a hydrocarbon, or an air freshener, the method comprising the steps of: placing a first product component into a container, the container comprising a valve dispensing port; adding a second product component into the container, the second product component comprising at least one of: (1) a solid form of the second product component and (2) a liquid form of the second product component; sealing the container; and warming, after the step of sealing, the second product component in the container at least ten degrees Celsius, where the step of warming results in a phase change of all of the second product component into a gas phase, at least a portion of the gas phase of the second product component dissolving into the first product component to form the dispensable substance.

This disclosure additionally provides compositions of nitrous oxide mixtures, and methods for using the same, including in food preparation to generate aerated food products and/or aerated compositions.

Generally, the generated compositions reduce the amount of nitrous oxide required versus traditional methods using pure nitrous oxide. For example, the compositions reduce the amount of nitrous oxide used to prepare an equivalent amount of aerated food product, while retaining aeration and at least one of and preferably all of volume, flavor, and an aroma profile. The mixtures and methods reduce the amount of nitrous oxide emissions generated in the preparation of various products.

Herein, a z-axis is aligned with gravity, where an x-axis and a y-axis form a plane perpendicular to the z-axis.

Figure 1A:
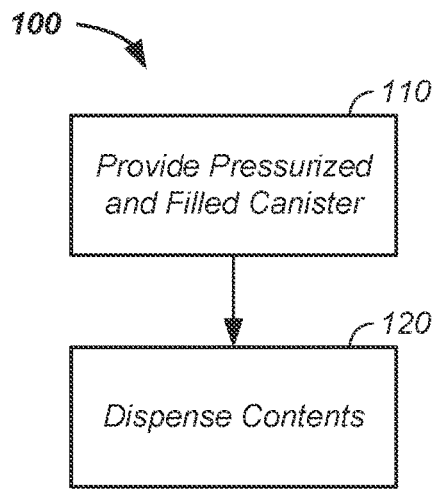
FIG. 1A and FIG. 1B illustrate a method of use of a pressurized container and whipped cream dispenser, respectively.

Referring now to FIG. 1A, a method of dispensing a product 100 from a pressurized container is illustrated. Generally, the method of dispensing a product 100 comprises the steps of providing a pressurized and product constituent filled container 110 and a step of dispensing contents 120 from the pressurized container.

Herein, without loss of generality and for clarity of presentation, food products and whipped cream are used as non-limiting examples of products dispensed by the taught apparatus and methods of use thereof. Again, for clarity of presentation and without loss of generality, examples are used for preparation, storage, and/or dispersion of the nitrous oxide mixtures, with particular examples to whipped cream. However, more generally, the invention relates to preparation, storage, and/or dispersion of any composition containing nitrous oxide and/or a second gas, such as a noble gas, from a pressurized container.

Figure 1B:
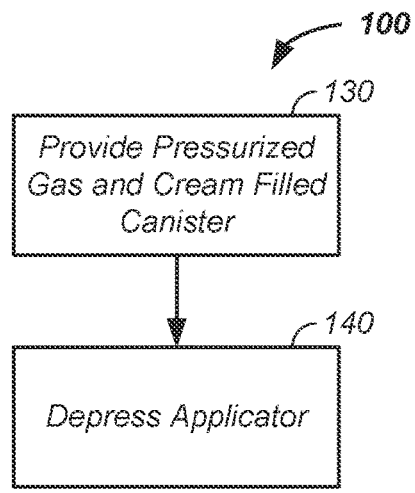

Referring now to FIG. 1B, the method of dispensing a product 100 is illustrated where steps include: providing a pressurized gas and cream filled canister 130 and depressing an applicator mechanism, such as a trigger or button, to dispense the product 140.

Figure 2:
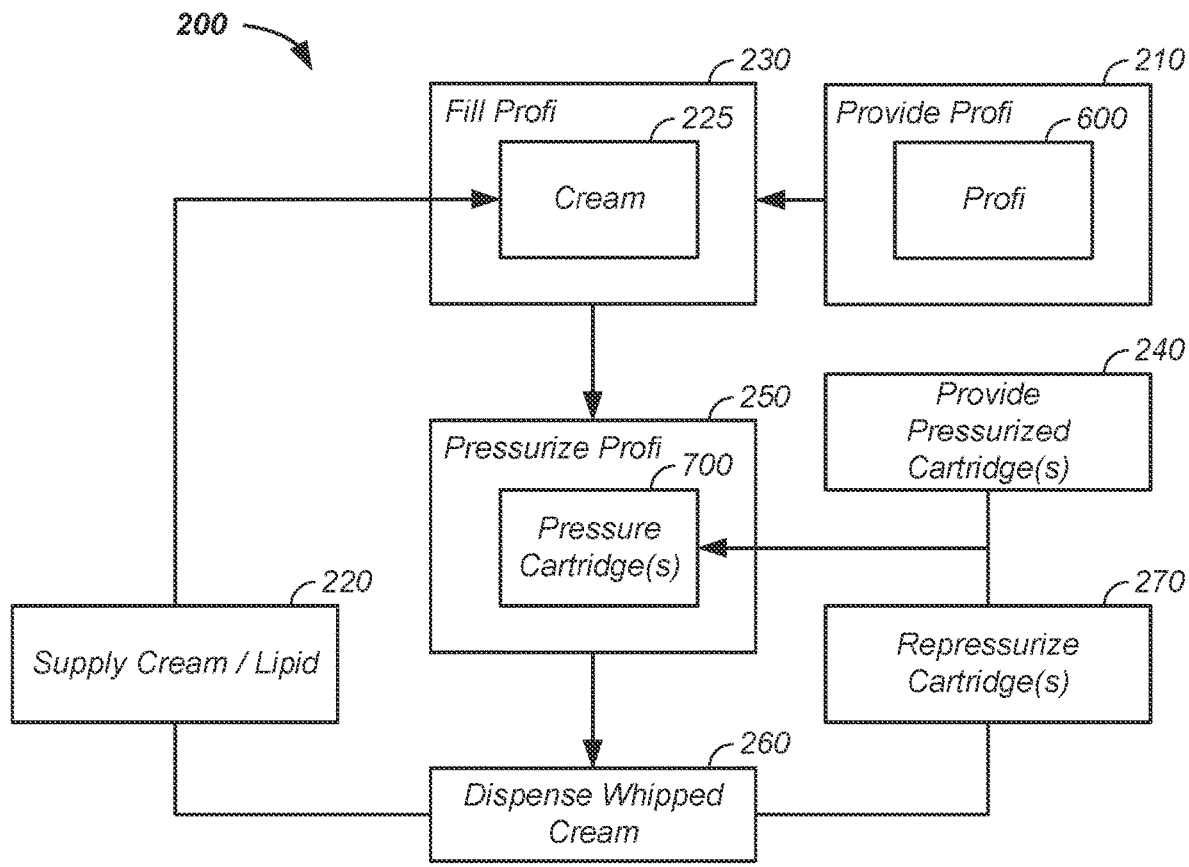
FIG. 2 illustrates assembly and use of a profi or reusable pressure vessel.
Figure 3:
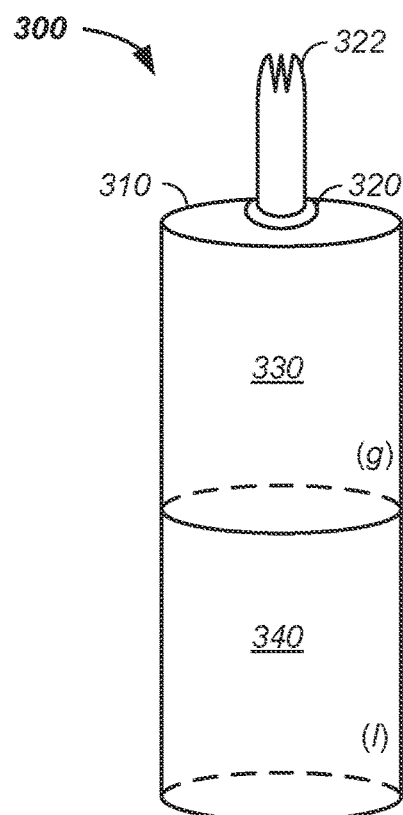
FIG. 3 illustrates a whipped cream canister.

Referring now to FIG. 1B, FIG. 2, and FIG. 3, a whipped cream canister 300 is distinguished from a profi 600. For example, the U.S. Department of Transportation (DOT) carefully regulates the pressure of shipped canisters, such as a whipped cream canister 300, such as purchased at a grocery store to contain a maximum pressure of 200 pounds per square inch (psi). Indeed, whipped cream canisters sold in grocery stores are governed by special permits limiting the canisters to 150 psi prior to leaving a production facility. Further, whipped cream is dispensed from the whipped cream canister 300 until one or more of the cream and the nitrous oxide in the whipped cream canister 300 is depleted. The whipped cream canister 300 is not refillable. In stark contrast, the profi 600 comprises a container containing, at initial dispensation of a product, a pressure in excess of 200 psi, such as above 200, 300, 500, 700, 740, 750, 760, 775, 1000, or 2000 psi. The profi 600 is optionally and preferably refillable, such as with cream 225 and the use of a removeable/replaceable pressurized cartridge 700. Optionally and preferably, the profi 600 is refilled and/or repressurized by an individual outside of a manufacturing facility, such as at a coffee shop, restaurant, or a personal residence.

Referring again to FIG. 2, a method of use of a profi 200 is illustrated. The method of use of a profi 600 includes one or more of the steps of: providing a profi 210, supplying a cream/lipid 220, filling the profi 230, such as with the cream 225, pressurizing the profi 250, and dispensing the whipped cream 260, or other product. Optionally and preferably, the method of use of the profi 200 includes one or more of the steps of: providing a pressurized cartridge 240 and/or repressurizing an already used cartridge 270 and using the pressure cartridge 700 in the step of pressurizing the profi 250. Stated again, a profi 600 is optionally charged with a new or refilled pressure cartridge 700. The pressure cartridge 700 is further described, infra.

A whipped cream canister 300 contains a maximum pressure of 200 psi and is a single use item, until one or more of the nitrous oxide and/or cream is dispensed. In stark contrast, a profi 600 uses a pressure cartridge 700 to charge the profi 600 with a gas containing nitrous oxide, where the pressure cartridge 700 and/or the profi is reusable. The pressure cartridge 700 includes an outer pressure wall 710 that contains an internal, typically pressurized, volume. The pressure cartridge optionally and preferably contains a pressure gas delivery port that connects to receiving/charging port of the profi 700. The pressure gas delivery port is optionally opened when charging the profi in either a temporary, permanent, or resealable manner, such as with a valve and/or a pressure regulator.

Referring now to FIG. 3, the whipped cream canister 300 is further described. The whipped cream canister includes a low pressure containment housing 310 and an interface 320 to an applicator tip 322. The low pressure containment housing 310 contains a gas volume, such as nitrous oxide 352, at a maximum pressure of 200 psi and a liquid volume 340, which included the cream 225. To dispense whipped cream 262 from the whipped cream canister 300, the interface 320 is temporarily opened, which allows the internal nitrous oxide 352 to dispense along with the cream 225. The sudden change in pressure from an internal pressure within the low pressure containment housing to a still lower atmospheric pressure causes dispensed nitrous oxide to expand, which expands the cream 225 into a form of whipped cream 262.

Referring now to FIGS. 4(A-C), constituents 400 of the low pressure whipped cream canister 300 and/or the profi 600 are described. For clarity of presentation and without loss of generality, as illustrated, the constituents 400 are contained in the low pressure containment housing 310. However, the constituents are optionally contained, in a high pressure containment housing 610 of the profi 600. In reference to the description of FIGS. 4(A-C), the term housing is used to refer to both the low pressure containment housing 310 of the whipped cream canister 300 and the high pressure containment housing 610 of the profi 600. Herein, the clause canister/cartridge refers to the whipped cream canister 300, the high pressure containment housing 610, and/or the pressure cartridge 700 used to charge the profi 600.

Pressurized Housing Gases

Figures 4A, 4B, 4C:
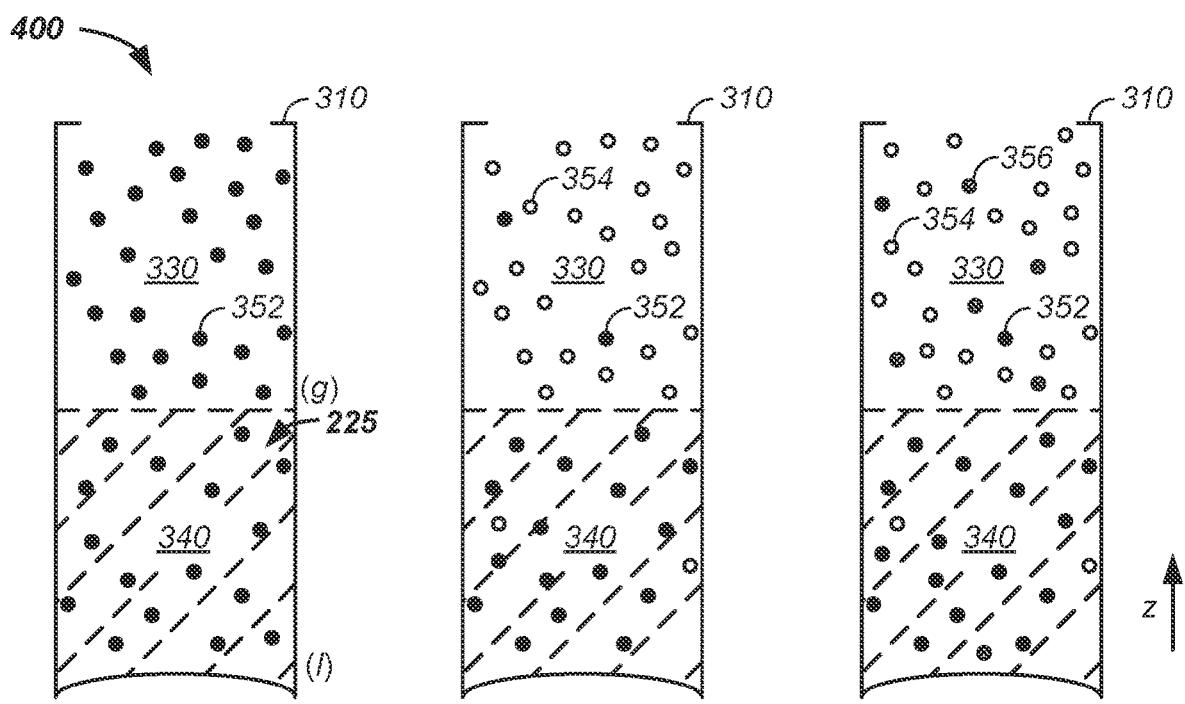
FIG. 4A, FIG. 4B, and FIG. 4C illustrate a pressure filled container containing one, two, and three gases, respectively.

Referring now to FIG. 4A, a first case of a single gas, such as nitrous oxide 352, and cream 225 in the housing is illustrated. In this first case, the constituents 400 in the housing include: a gas volume 330 and a liquid volume 340. The gas volume 300 contains nitrous oxide 352. The liquid volume 340 contains the cream 225 and nitrous oxide 352 dissolved in the cream 225. In this first case, nitrous oxide is at least 95, 96, 97, 98, 99, 99.5, and/or 99.9 percent of the gas in the housing. The balance of the gas is outgassing from the cream and/or impurities, in the nitrous oxide and/or ambient air, making their way into the housing in a manufacturing step.

Referring now to FIG. 4B, a second case of two gases, such as nitrous oxide 352 as a first gas and a second gas, along with cream in the housing is illustrated. In this second case, the constituents 400 in the housing still include: a gas volume 330 and optionally a liquid volume 340. The gas volume 330 includes a first gas, such as nitrous oxide, and a second gas intentionally introduced into the housing, not an accidental inclusion of atmospheric gas, during a pressurization of the housing step. For example, the first gas and the second gas are intentionally used to charge the whipped cream canister 300 at a manufacturer or the first gas and the second gas are intentionally introduced in the profi pressurization step 250, described supra. The first gas is optionally and preferably nitrous oxide 352. The second gas is ambient air, such as air in the earth's atmosphere, hydrogen, helium, nitrogen, carbon dioxide, neon, argon, krypton, or xenon. A preferred second gas is argon. Relative partial pressures, volumes, mol content, and/or concentrations of the first gas and second gas are further described, infra. In this second case, environmental air is not intentionally introduced into the housing, but may make up an impurity of up to 3, 2, 1, 0.5, 0.25, 0.1, or 0.01 percent by volume and/or by mass.

Figure 6A:
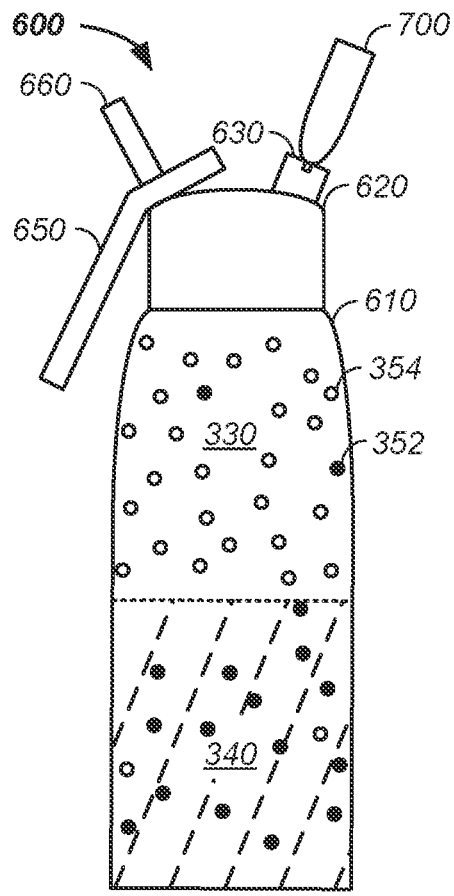
FIG. 6A and FIG. 6B illustrate profis.

Still referring to FIG. 4B, the two gases introduced into the housing are further described in terms of the presence of the cream 225. For clarity of presentation and without loss of generality, the first gas in this example is nitrous oxide 352 and the second gas is a noble gas, such as argon 354. Nitrous oxide 352 is soluble in fats and/or lipids, such as are present in the cream 225. Argon 354 is relatively insoluble in the cream 225. Thus, as illustrated, the concentration of nitrous oxide 352 falls in the gas volume 330 above the cream 225 while the argon 354 remains in high concentration in the gas volume 330/headspace of the container. As a result, inhalant abuse or huffing of the nitrous oxide through dispensing the gases from the housing in an upright position, a proper inverted position is used to dispense whipped cream, is ineffective for a high as the nitrous oxide concentration in the headspace is diminished as the nitrous oxide resides in the cream 225. Discussion of the percentage of nitrous oxide in the headspace and cream are provided, infra. In this second example, the pressurized argon 354 functions to eject the cream 225 and dissolved nitrous oxide when the housing is used in a proper inverted orientation, where the liquid volume 340 covers an entrance to a delivery port, such as a dispensing port. In FIG. 6A, further described infra, the dispensing port 660 is further described.

In FIG. 3, the dispensing port of the whipped cream canister 300 is the an exit through which the cream 225 passes during use to atmosphere, such as through the interface 320 and the applicator tip 322.

Referring now to FIG. 4C, three gases are optionally introduced into the housing, canister, and/or cartridge. For clarity of presentation and without loss of generality, in this example the first gas is nitrous oxide 352, the second gas is argon 354, and the third gas is nitrogen 356, though any gases are optionally used. As illustrated, the nitrous oxide permeates/dissolves into the cream 225/liquid volume 340/liquid phase while the argon 354 and the nitrogen 356 remain primarily in the headspace/gas volume 330. Further, the analgesic effect of nitrous oxide follows a logarithmic scale, thus reducing nitrous oxide in the headspace above the cream is significantly amplified when it comes to reduction in the analgesic effect for the huffer. As a result, if huffed, the huffer is huffing the non-high inducing gases of argon 354 and nitrogen 356, while if the canister/cartridge is properly inverted, the whipped cream is dispensed as the product is intended. Generally, any number n of gases are introduced into the canister/cartridge/profi, where n is a positive integer, such as 2, 3, 4, 5, 6, 7, or more. Optionally and preferably, the concentration of each gas is greater than 0.001, 0.01, 0.1, 1, 2, or 3 percent. Generally, a preferred concentration of each gas exceeds the concentration of that gas in the earth's atmosphere as adjusted for pressure. Stated again, generally the second, third, fourth, . . . , $n^{th}$ gas is present at a concentration above atmospheric air compressed to the pressure in the canister, cartridge, and/or low pressure containment housing 310 of the whipped cream canister 130, the high pressure containment housing 610, and/or the profi 600. Hence, the concentration of each gas in the canister/cartridge exceeds a concentration obtained through the accidental inclusion of atmospheric air in the manufacturing/pressurization/charging process, such as in the step of providing a pressurized gas and cream filled canister 130 and/or the step of pressurizing the profi 250.

Optionally, the filled canister 130 is a sealed can/soda can/beverage can, such as dispensed from a vending machine, which is opened by the user just prior to drinking a contained beverage. For instance, the act of opening the sealed can uses a pop top or a lid that is removed by unscrewing a cap. Generally, the sealed can is packaged using any of the 1, 2, 3, or more gases, described supra, in combination with the beverage, where the 1, 2, 3, or more gases are optionally and preferably dissolved into the beverage at time of production and form a headspace, such as in equilibrium with the beverage prior to the user opening the sealed can.

Atmospheric and Compressed Atmosphere Concentration of Gases

This section details maximum atmospheric gas concentrations intentionally and/or accidentally introduced as an impurity into the canister/cartridge.

The Earth's atmosphere is at one atmosphere (atm) pressure. Atmosphere is optionally placed in the low pressure containment housing 310 of the whipped cream canister 130 or the high pressure containment housing 610 of the profi 600 as an impurity and/or is intentionally used as one of the one or more pressurizing gases. In any case, the maximum amount of any environmental air constituent is a multiple of the environmental air concentration, where the multiple is the maximum pressure in atmospheres in the housing at time of filling. A relationship of housing pressure to atmospheres is provided in Table 1.

TABLE 1

Canister and Cartridge Pressures

| Housing Type | Condition | psi | atm |
| --- | --- | --- | --- |
| Canister | Initial Filling Pressure | 175 | 11.9 |
| Canister | Maximum Pressure* | 200 | 13.6 |
| Cartridge | N$_2$O phase change minus 25 psi | 725 | 49 |
| Cartridge | N$_2$O phase change | 750 | 51 |
| Cartridge | N$_2$O phase change plus 25 psi | 775 | 53 |
| Cartridge | Optional Filling Pressure | 1,000 | 68 |
| Cartridge | Optional Filling Pressure | 2,000 | 136 |

*as allowed by the U.S. Department of Transportation

It follows, that the maximum concentration of a component of the atmosphere in the whipped cream canister 130 or high pressure containment housing 610 is the atmospheric concentration times the initial atmospheric pressure of the whipped cream canister 130 or high pressure containment housing 610.

The Earth's atmosphere contains many components. The concentration of selected gases in the Earth's atmosphere is provided in Table 2 along with the maximum pressure of the component at 200 psi or 13.6 atm, the highest pressure of the whipped cream canister 300 allowed to be shipped by the U.S. Department of Transportation. For instance, the highest possible pressure of xenon in the whipped cream canister 130 by compressing atmospheric air into the canister is 1.18 ppm (0.087 ppm*13.6) at 200 psi or 13.6 atm, the highest pressure allowed by the U.S. Department of Transportation. Thus, a concentration of greater than 1.18 ppm xenon in the whipped cream canister 13.6 means that the manufacturer had to purposely add xenon to the canister, where the added gas containing xenon has a xenon concentration higher than naturally occurring xenon concentration in air/atmosphere. Like calculations reveal if the compressed gas used to fill the whipped cream canister 130 or profi 600 exceeds concentrations found in earth's atmosphere.

TABLE 2

Atmospheric and Compressed Atmospheric Gas Concentrations.

| Gas | Atmospheric Concentration (Percent) | Atmospheric Concentration (ppm) | Concentration at 13.6 atm (ppm) |
|---|---|---|---|
| Nitrogen | 78.084 | 780,790 | 10,618,744 |
| Oxygen | 20.946 | 209,445 | 2,848,452 |
| Argon | 0.934 | 9,339 | 127,010.4 |
| Carbon Dioxide | 0.041 | 404 | 5,490 |
| Neon | 0.0018 | 18.21 | 247 |
| Helium | 0.00052 | 5.24 | 71.3 |
| Krypton | 0.0001 | 1.14 | 15.5 |
| Hydrogen | 0.00005 | 0.5 | 6.8 |
| Methane | 0.000187 | 0.5 | 6.8 |
| Xenon | 0.0000087 | 0.087 | 1.18 |

Several examples are provided as to the contents of the cartridge/canister and/or the profi 600.

Example I

Referring still to FIG. 4C and Table 2, in a first example: for two, three, four, or more gases introduced into the cartridge/canister whipped cream canister 130, and/or the profi 600, an optional and preferred concentration of each gas is greater that the concentration of each respective gas in the atmosphere at 200 psi or 13.6 atm of pressure, as listed in column 4 of Table 2.

Example II

Referring again to FIG. 4B, in a second example, for two gases introduced into the cartridge/canister whipped cream canister 130, and/or the profi 600, optionally and preferably, the first gas is nitrous oxide and the second gas is air or the first gas is nitrous oxide and the second gas is selected from column 1 of Table 2.

Example III

Referring again to FIG. 4C, in a third example, three, four, or more gases are introduced into the cartridge/canister whipped cream canister 130, and/or the profi 600, where optionally and preferably the first gas is nitrous oxide, the second gas is selected from column 1 of Table 2, and the third gas is selected from column 1 of Table 2.

Example IV

Referring again to FIG. 4C, in a fourth example, for three, four, or more gases introduced into the cartridge/canister whipped cream canister 130, and/or the profi 600, optionally and preferably the first gas is nitrous oxide, the second gas is selected from column 1 of Table 2, and the third gas is air.

Example V

Referring again to FIG. 4C, in a fifth example, for four or more gases introduced into the cartridge/canister whipped cream canister 130, and/or the profi 600, optionally and preferably, the first gas is nitrous oxide, the second gas is selected from column 1 of Table 2, the third gas is selected from column 1 of Table 2, and the fourth gas is air.

Proper/Improper Use of Canister/Cartridge

Figure 5A:
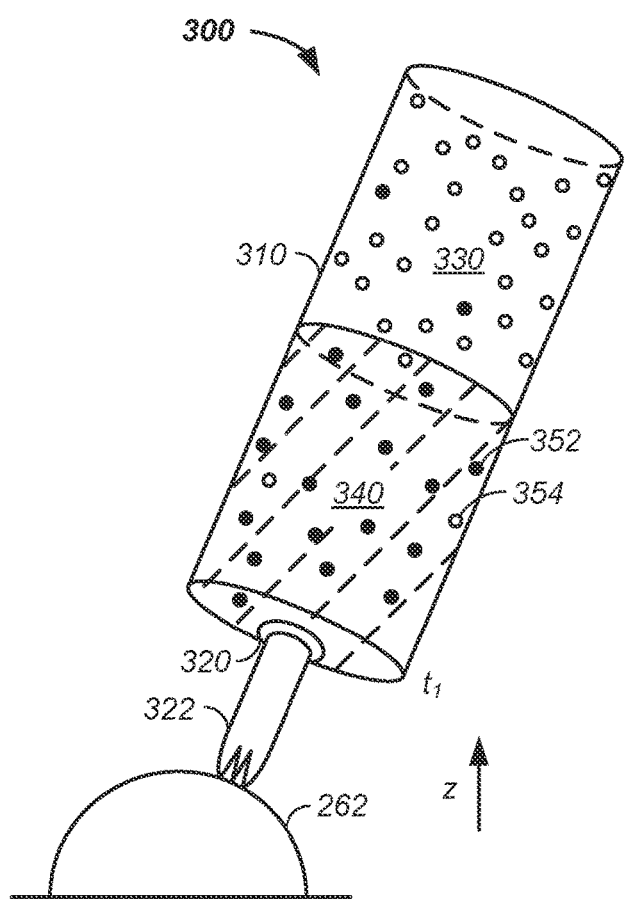
FIG. 5A and FIG. 5B illustrate a pressurized container in two orientations.
Figure 5B:
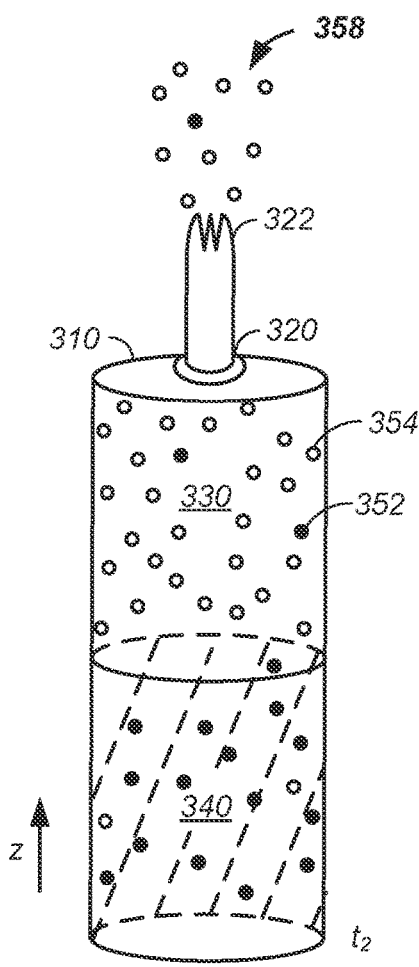

Referring now to FIG. 5A and FIG. 5B, the whipped cream canister 300 is illustrated in a proper whipped cream dispensing orientation and an improper huffing orientation, respectively. In both the dispensing orientation and the huffing orientation, the liquid volume 340 is pulled by gravity, z-axis, downward and the lower density gas volume 330 rises above the lower liquid volume. Thus, referring now to FIG. 5A, when the whipped cream canister 300 is orientated in the dispensing orientation and the can is activated, opened to atmosphere via the applicator tip 322, whipped cream 262 is dispensed via the dispensing port immersed in the liquid volume 340. Further, referring now to FIG. 5B, when the whipped cream canister 300 is orientated in a huffing orientation, where the dispensing port is immersed in the air volume 330, the less dense gas volume 330 is dispensed. As illustrated, in the huffing orientation, the nitrous oxide is dissolved into the cream in the liquid volume 340 and the gas volume 330 is dominated by the non-soluble gas, argon 354. More generally, the gas volume 340 contains any one, two, three, or more of nitrogen, oxygen, argon, carbon dioxide, neon, helium, krypton, hydrogen, methane, xenon, atmosphere, and a noble gas, while the high inducing nitrous oxide remains dominantly dissolved in the cream 225 and/or is in the liquid volume, such as more than 50, 60, 70, 80, 90, or 95 percent of the nitrous oxide, by mass. FIG. 5A and FIG. 5B illustrate the gas volume 330 rising above the liquid volume 340; the same logic of dispensing whipped cream in the inverted dispensing orientation and dispensing non-high inducing gases in the upright huffing orientation is applied to the high pressure containment housing 610 or the profi 600.

Profi

Figure 6B:
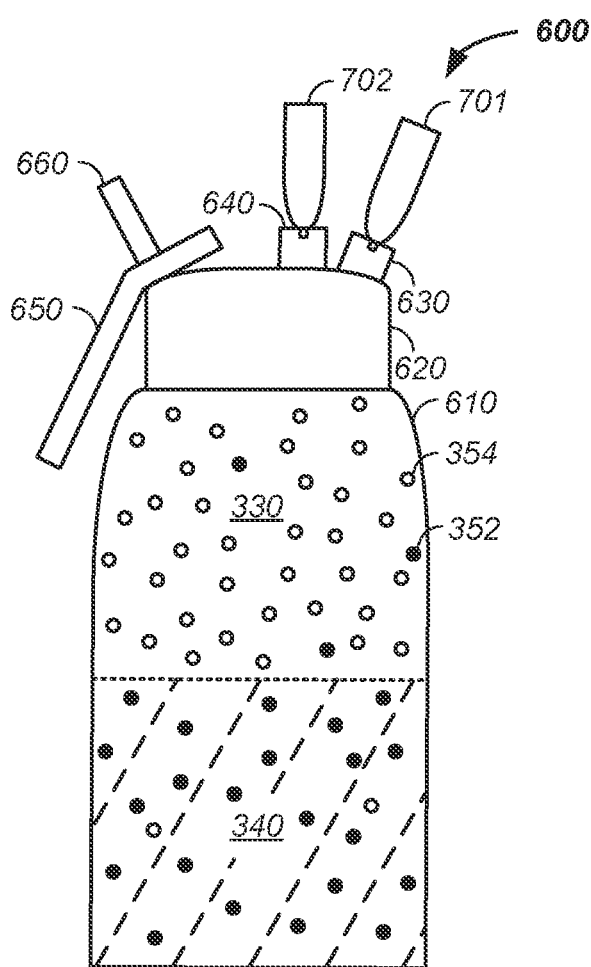
Figure 7:
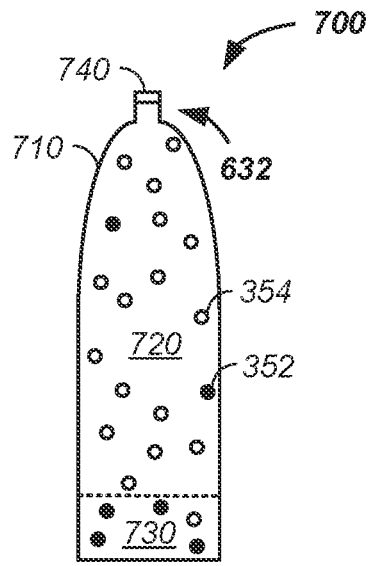
FIG. 7 illustrates a pressurized cartridge.

Referring now to FIG. 6A, FIG. 6B, and FIG. 7, the profi 600 is further described. Generally, as described, supra, the profi 600 includes a high pressure containment housing 610 that is pressurized using a replaceably attached pressure cartridge 700, such as attached by an end user. During use, cream 225 in the liquid volume 340 of the high pressure containment housing 610 is dispensed when the profi 600 is held in an inverted dispensing orientation and the high pressure containment housing 610 is temporarily opened to a lower pressure, such as atmospheric pressure, such as via the dispensing port.

Referring now to FIG. 6A, the pressure containment elements of the profi 600 are further described. Generally, the high pressure containment housing 610 of the profi 600 contains the liquid volume 340, such as the cream 225 and dissolved nitrous oxide as described above, and the gas volume 330, such as the less soluble gases of argon, nitrogen, and the like as described above. Before pressurization, the liquid contents of the profi are added, such as the cream 225 and any optional additive as further described, infra. As illustrated, the high pressure containment housing 610 is attached to a lid 620, such as a removable lid attached as a thread on lid. Optionally, the lid is hingedly attached to the high pressure containment housing. Generally, the high pressure containment housing 610 contains any sealable/resealable opening for adding the contents, such as the cream 225.

Still referring to FIG. 6A and referring again to FIG. 7, the pressurization elements of the profi 600 are further described. Generally, the pressure cartridge 700 is attached to the profi 600 and the higher pressure in the pressure cartridge 700 is equalized with the lower pressure in the now sealed profi 600, lid 620 sealed to high pressure containment housing 610. As illustrated, the pressure cartridge 700 is attached to a receiving port 630, which opens the contents of the pressure cartridge 700 to an interior volume of the profi 600. The sealing port 620 is optionally attached with a lock and key interface, such as a physical key shape of an end of the pressure cartridge 600 inserts into a lock element of the receiving port 630 or vise-versa. Similarly, an end or element of the pressure cartridge 600 screws into the receiving port 630 of the profi 600. Similarly, a slip connection and/or a regulator are optionally used as part of the receiving port. Generally, any attachment, physical interface, and/or accessory used to deliver gas(es) from the pressure cartridge 700 to the profi 600 is used as the receiving port 630. As illustrated, a valve 740 couples the receiving port 620 to the pressure cartridge 700. The valve 740 is optionally and preferably a pneumatic style valve, such as a Schrader valve. The valve 740 is optionally a one-way valve, which prevents flow of the cream 225 from the profi 600 into the pressure cartridge 700, which eases the process of repressurizing the cartridge 270 for reuse. The valve 740 is optionally affixed to the receiving port 620 and the pressure cartridge 700 is brought into contact with the valve 740 in the process of pressurizing the profi 250. Optionally and preferably, the pressure cartridge 700 is detached from the profi 600 in a step prior to the step of dispensing the whipped cream 260.

Still referring to FIG. 6A, the pressure cartridge 700 is optionally connected to a side or a bottom of the profi 600, which allows a gas or multiple gases from the headspace above a liquid in the pressure cartridge 700 to pass into the profi 600 without the liquid from the pressure cartridge 700 passing into the profi 600. For instance, nitrous oxide gas above a nitrous oxide liquid in the pressure cartridge 700 is passed into the profile, such as through a pressure charging port/valve.

Still referring to FIG. 6A, the dispensing elements of the profi 600 are further described. Generally, the profi includes a product dispensing port 660 and a trigger 650 for alternatingly opening and closing the dispensing port 660. As illustrated, the trigger 650 is a squeezable handle that when pulled on by the fingers of a hand grasping a handheld version of the profi 600 opens a dispensing valve in the dispensing port and by relaxing pressure on the handle, the dispensing valve is shut. When the dispensing valve is opened, the cream 225 and at least the nitrous oxide 352 are dispensed, where the nitrous oxide 352 introduced into the lower pressure of normal atmospheric pressure expands to form the whipped cream 262. Generally, the dispensing elements of the profi 600 include any trigger, button, and/or mechanical mechanism opening a path through the dispensing port 660 to allow passage of one or more contents in the profi 600 to a volume outside of the profi 600.

Optionally, the receiving port 620 is integrated into the dispensing port 660 where the pressure cartridge 700 is used to pressurize/charge the profi 600, the pressure cartridge is removed after a first seal is closed and the first seal and/or a second seal is mechanically/electromechanically opened, such as triggered by a button or lever, resultant in at least one content of the profi 600 being released through the first and/or second seal to an environment outside of the profi 600.

Referring again to FIG. 6B, the profi 600 is illustrated with a first receiving port 630 and a second receiving port 640, where the first and second receiving ports 630, 640 respectively attach to a first and second pressure cartridge 701, 702. Referring still to FIG. 6B and referring again to FIG. 6A, optionally and preferably the first pressure cartridge 701 is used to pressurize the profi 600 through the first receiving port 630 and, after detaching the first pressure cartridge 701 from the first receiving port 630, the second pressure cartridge 702 is used to further pressurize the profi through the first receiving port 630. Generally, the profi 600 contains any number m and n of receiving ports 630 and dispensing ports 660, respectively, where m and n are positive integers of 1, 2, 3, or more. Optionally and preferably the receiving port 630 is specified for pressures of 200, 300, 750, 1000, 2000, 3000, or more psi and the dispensing port operates at pressures up to 150, 175, or 200 psi. Optionally, any number of pressure cartridges 700 are sequentially used to pressurize the profi 600, such as for a single batch of cream 225, as further described infra.

Mixed Pressure Cartridges

Still referring to FIG. 6A, FIG. 6B, and FIG. 7, pressurizing the profi 600 with 1, 2, 3, or more mixed gas pressure cartridges and/or 1, 2, 3, or more single gas profi cartridges is described. Generally, if it is desired to pressurize the profi 600 with two or more gases, then the two or more gases are optionally provided in a single pressure cartridge or a first gas is introduced into the profi 600 via a first pressure cartridge 701 and a second gas is introduced into the profi 600 via a second pressure cartridge 702, either sequentially, such as via a single receiving port or in parallel via two receiving ports. Examples are used to describe the process of pressurizing the profi 250.

Example I

In a first example, it is desired to charge the profi 600 with two gases, such as nitrous oxide and nitrogen at a desired ratio. In a first case, the profi 600 is charged with a pressure cartridge 700 containing the desired ratio, as measured by partial pressures, moles, and/or mass, of nitrous oxide and nitrogen. In a second case, the profi 600 is pressurized through sequential attachment of a first pressure canister 701, such as filled with one of nitrous oxide or nitrogen, and attachment of a second pressure canister 702, such as the remaining element of nitrous oxide and nitrogen not in the first pressure container 701. In the second case, the desired ratio of the nitrous oxide and nitrogen is obtained by partial pressures, moles, and/or mass and/or through use of a first pressure in the first pressure container 701 and a second pressure in the second container differing from the first pressure by at least 0, 1, 2, 3, 4, 5, 10, or 15 percent. In a third case, the profi 600 is charged in parallel with a first pressure container 701 containing a first gas, such as nitrous oxide, connected to the first receiving port 630 and a second pressure container 701 containing the second gas, such as nitrogen, connected to the second receiving port. In the second and third cases, standard chemistry/physics equations relating pressure and concentration to volume are used to obtain the desired ratio/concentration/content of nitrous oxide and nitrogen, as measured by mass, percent volume, moles, and/or partial pressure. Naturally, any two gases are substituted for nitrous oxide and nitrogen in this example. Further, extension of this example allows pressurization of the profi 600 with 3, 4, 5 or more gases and/or air through 1 or more pressurization ports. In the described manner, the amount of each of a first gas, a second gas, a third gas, . . . , and/or an $n^{th}$ gas at time of pressurization is adjustable from 0 to 100 percent of the introduced gas, such as greater than 0, 1, 2, 3, 4, 5, 10, 15, 20, 25, 30, 35, 40, 45, 50, 60, 70, 80, or 90 percent of a given gas and less than 100, 99, 98, 97, 96, 95, 90, 80, 70, 60, 50, 40, 30, 20, or 10 percent of the given gas, such as any gas listed in Table 2.

Pressure Cartridge with Liquid Phase

Figure 8:
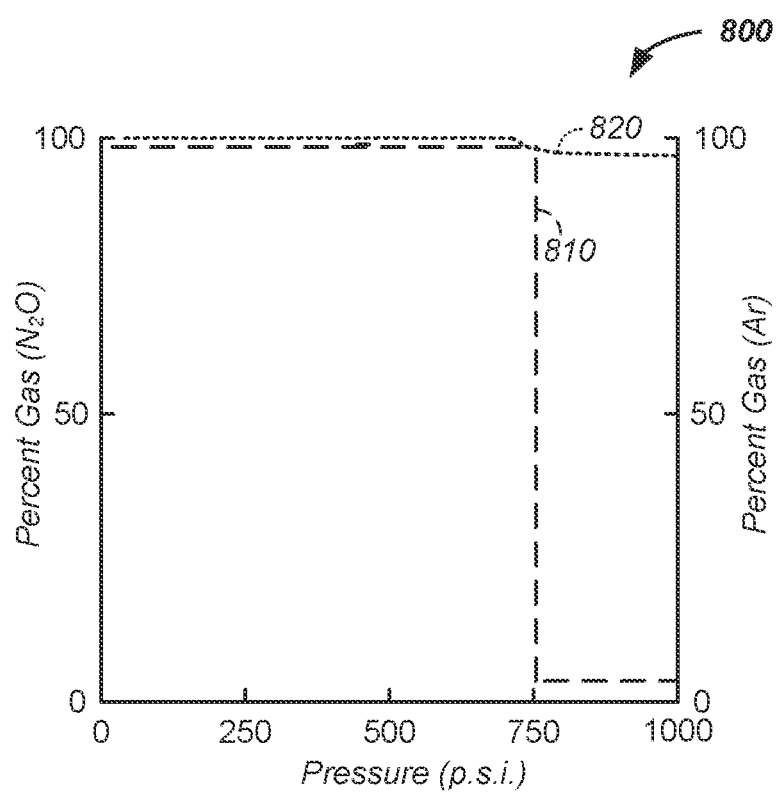
FIG. 8 illustrates a phase change of nitrous oxide.
Figure 9:
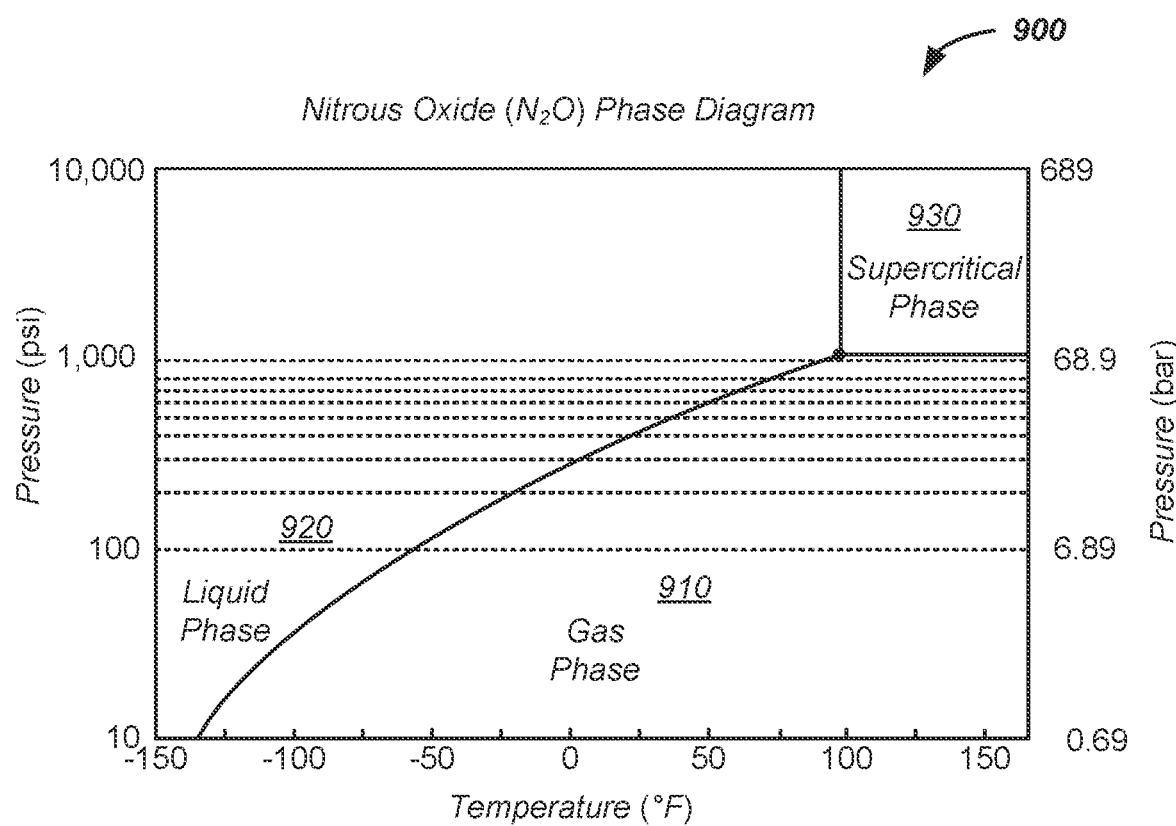
FIG. 9 illustrates a nitrous oxide phase diagram.

Referring again to FIG. 7 and referring now to FIG. 8 and FIG. 9, a pressure cartridge 700 containing a liquid form of one or more gases is described. For clarity of presentation and without loss of generality, nitrous oxide is used in examples of a pressure cartridge containing at least a liquid form of an atom or molecule that is a gas at standard temperature, 25° C., and pressure, 1 atm, though any one or more gases are optionally present in the pressure cartridge 700 in the form of a gas and/or a liquid. Referring now to FIG. 8, at pressures exceeding 750 psi, nitrous oxide is present as a liquid, while argon is still in a gas form from at least 750 to 1000 psi.

Referring still to FIG. 7, nitrous oxide 352 and argon 354 are in the pressurized cartridge 700. Further, as illustrated, the pressure in the pressurized cartridge has forced the nitrous oxide 352 to be at least in a liquid phase, such as in a liquid fraction 730 inside the pressurized container, and to optionally be in a gas phase, in a headspace gas fraction 720 inside the pressurized cartridge 700.

Referring now to FIG. 9, a nitrous oxide phase diagram 900 is presented. Notably, nitrous oxide transitions from a nitrous oxide gas phase 910 to a nitrous oxide liquid phase 920 at a pressure exceeding 750 psi at room temperature and is in a nitrous oxide supercritical phase 930 above 1000 psi, FIG. 9.

The pressure cartridge 700 is optionally maintained at a temperature and pressure where the nitrous oxide is in the form of a solid, liquid, or a supercritical fluid. When two or more gases are present in the pressure cartridge, the temperature and pressure are optionally set where each of the two or more gases are in a solid, liquid, or supercritical phase.

Figure 10:
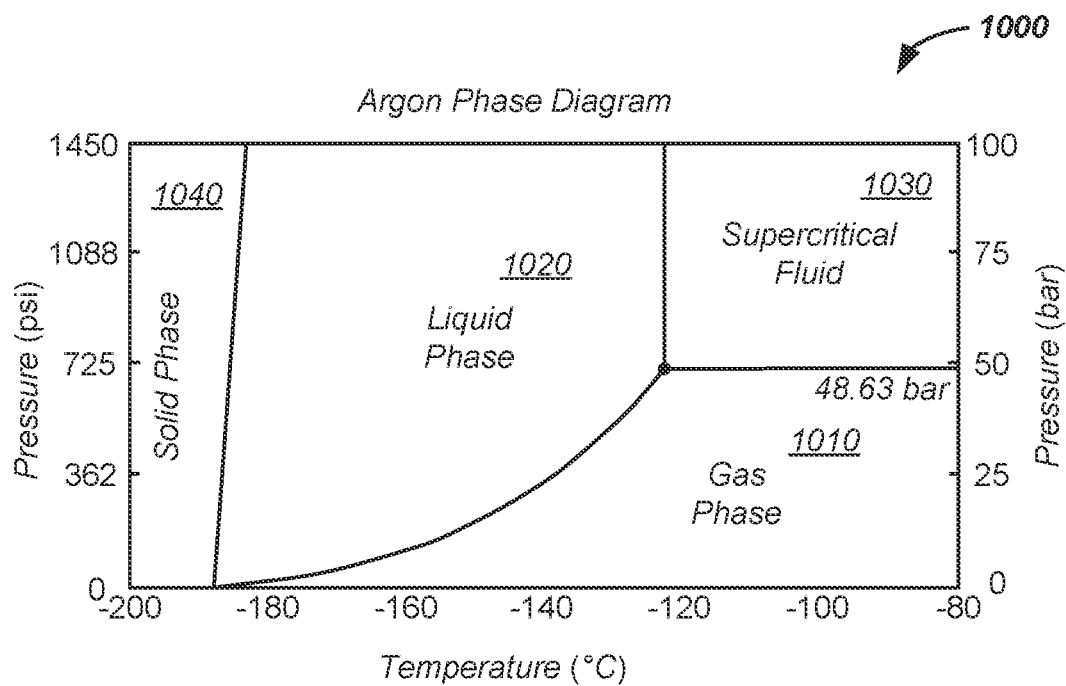
FIG. 10 illustrates an argon phase diagram.

Referring now to FIG. 10, an argon phase diagram 1000 is illustrated. As illustrated, argon is present in an argon gas phase 1010, an argon liquid phase 1020, an argon supercritical phase 1030, or an argon solid phase 1040 as a function of temperature and pressure.

Referring again to FIG. 9 and FIG. 10, nitrous oxide and argon are in different phases at some temperatures and pressures. However, nitrous oxide and argon are in the same phase at other temperatures and pressures, which facilitates manufacture of a two gas container, as further described infra.

Multi-Gas Pressurized Container

Figure 11:
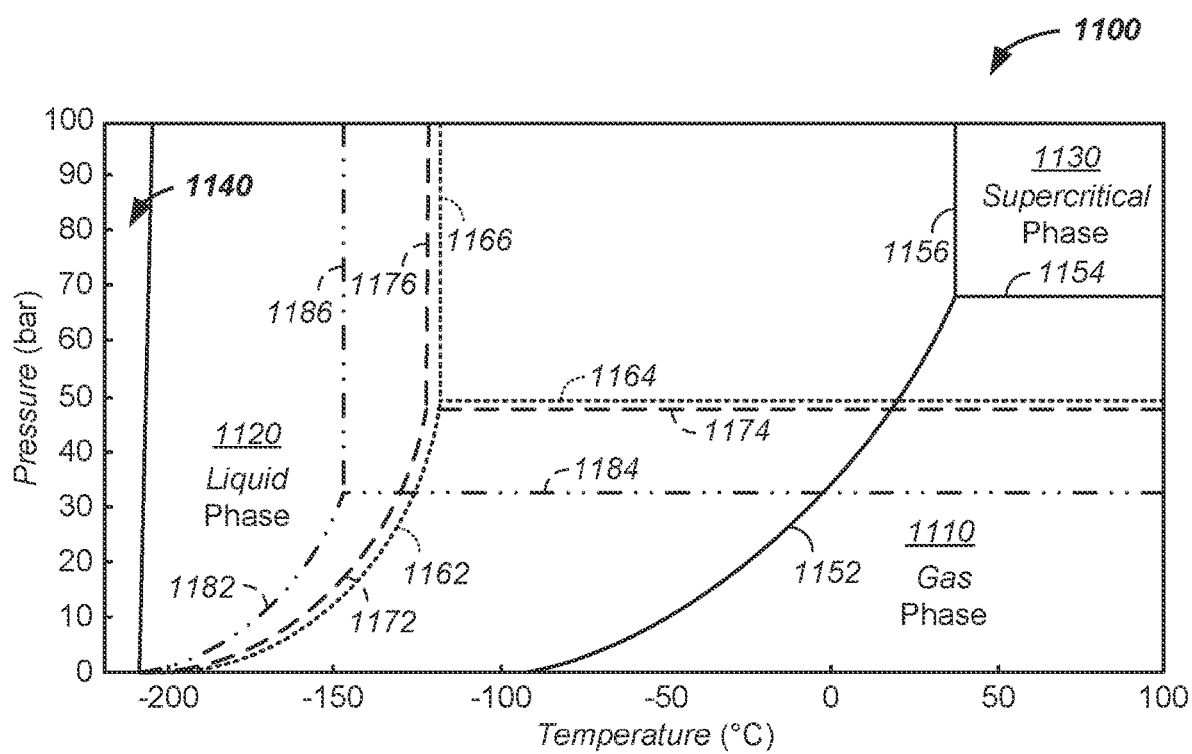
FIG. 11 illustrates multiple phase diagrams.
Figure 12:
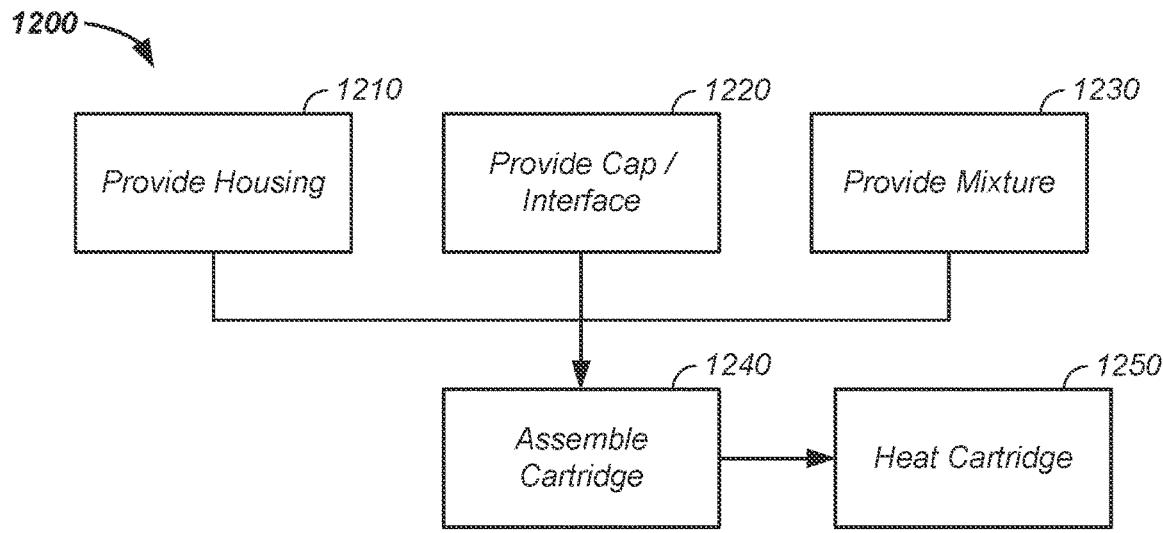
FIG. 12 illustrates a method of assembling a cartridge.

Referring now to FIG. 11, a multi-chemical phase diagram 1100 is provided. Herein, an apparatus comprising a container filled with two or more gases, a method of manufacture of the multi-gas containing container, and a method of use of the multi-gas containing container is described.

There exist many applications of mixed gas use. In a first example, in a dental office anesthesia of a patient is achieved by delivering nitrous oxide and oxygen. In a second example, in deep sea diving a mix of oxygen and a second gas such as helium and/or argon is used to prevent the bends. In a third example, tungsten inert gas (TIG) welding uses argon gas and hydrogen gas. In each of these cases, the gases are traditionally provided in separate containers and are mixed at time of use, such as through one or more regulators, which have inherent risks and expense. As described herein, delivery of the two or more gases in each of these examples is optionally and preferably from a single container containing the mixed gases. Herein, for clarity of presentation and without loss of generality, mixtures of nitrous oxide and a second gas, such as described supra in the preparation of a whipped topping, are used to describe a multi-gas pressurized container, a method of manufacture of a container pressurized with multiple gases, and a method of use of a container filled with multiple gases. Generally, the container, a method of manufacture of the container, and use of the container includes any number of gases in a single container, such as n gases, where n is a positive integer of greater than 1, 2, 3, 4, 5, 6, 7, 8, 9, or 10. Optional gases in the two or more gas mixture include any two of more of: nitrous oxide, ambient air, such as air in the earth's atmosphere, hydrogen, helium, nitrogen, oxygen, carbon dioxide, methane, neon, argon, krypton, or xenon. Generally, each atom or molecule is in a given phase at a given temperature and pressure, such as nitrous oxide is: (1) a gas at a first temperature-pressure combination, (2) a liquid at a second temperature-pressure combination, (3) a supercritical fluid at a third temperature-pressure combination, or (4) a solid at a fourth temperature-pressure combination. Hence, each atom, molecule, or gas is herein referred to as a chemical.

Referring again to FIG. 11, the multi-chemical phase diagram 1100 is further described. As illustrated, the multi-chemical phase diagram 1100 provides overlapped phase diagrams for nitrous oxide (solid line), molecular oxygen or $O_2$ (dotted line), argon (dashed line), and nitrogen gas or $N_2$ (alternating solid and double dotted line). Herein, the nitrous oxide, molecular oxygen, argon, and molecular nitrogen each exist in a gas phase 1110, a liquid phase 1120, a supercritical phase 1130, or a solid phase 1140.

Still referring to FIG. 11, nitrous oxide phases and phase changes are described as a function of temperature and pressure. Nitrous oxide changes from: a gas to a liquid at a nitrous oxide gas-to-liquid interface 1152, from a gas to a supercritical fluid at a nitrous oxide liquid-to-supercritical fluid interface 1154, and from a liquid to a supercritical fluid at a nitrous oxide liquid-to-supercritical fluid interface 1156. For example, at a pressure exceeding 72.45 bar and a temperature exceeding 36.4 degrees Celsius, nitrous is in a supercritical phase. Similarly, at temperatures greater than −100° C., nitrous oxide is in a liquid phase at temperatures and pressures above and/or to the left of the nitrous oxide gas-to-liquid interface 1152. Generally, the phase of nitrous oxide is determined using a combination of temperature and pressure.

Still referring to FIG. 11, molecular oxygen phases and phase changes are described as a function of temperature and pressure. Molecular oxygen changes from: a gas to a liquid at a molecular oxygen gas-to-liquid interface 1162, from a gas to a supercritical fluid at an molecular oxygen gas-to-supercritical fluid interface 1164, and from a liquid to a supercritical fluid at a molecular oxygen liquid-to-supercritical fluid interface 1166. For example, at a pressure exceeding 50.4 bar and a temperature exceeding −118.57 degrees Celsius, molecular oxygen is in a supercritical phase. Similarly, molecular oxygen is in a liquid phase at pressures above the molecular oxygen gas-to-liquid interface 1162 and is in a supercritical phase at pressures above the molecular oxygen liquid-to-supercritical phase 1164.

Still referring to FIG. 11, argon phases and phase changes are described as a function of temperature and pressure. Argon changes from: a gas to a liquid at an argon gas-to-liquid interface 1172, from a gas to a supercritical fluid at an argon gas-to-supercritical fluid interface 1174, and from a liquid to a supercritical fluid at an argon liquid-to-supercritical fluid interface 1176. For example, at a pressure exceeding 48.63 bar and a temperature exceeding −122.46 degrees Celsius, argon is in a supercritical phase. Similarly, at pressures above the argon gas-to-liquid phase change 1172, argon is in a liquid state. Again, the phase of argon is determined by controlling temperature and pressure.

Still referring to FIG. 11, molecular nitrogen phases and phase changes are described as a function of temperature and pressure. Molecular nitrogen changes from: a gas to a liquid at a molecular nitrogen gas-to-liquid interface 1182, from a gas to a supercritical fluid at an molecular nitrogen gas-to-supercritical fluid interface 1184, and from a liquid to a supercritical fluid at a molecular nitrogen liquid-to-supercritical fluid interface 1186. For example, at a pressure exceeding 33.958 bar and a temperature exceeding −146.96 degrees Celsius, molecular nitrogen is in a supercritical phase. The phase of molecular nitrogen is determined by controlling temperature and pressure.

Still referring to FIG. 11, each of nitrous oxide, molecular oxygen, argon, and molecular nitrogen exist in a solid phase, such as at temperatures below −90.86, −218.79, −187.68, and −210.00 degrees Celsius, respectively.

Still referring to FIG. 11, there exists a range of temperatures and pressures where two or more chemicals are in a common phase and/or are two phases that mix. In a first case, a first chemical is in a gas phase and a second chemical is in a gas phase, which form a homogenous mixture. In a second case, a first chemical is in a liquid phase and a second chemical is in a liquid phase, which form a homogenous mixture. In a third case, a first chemical is in a liquid phase and a second chemical is in a supercritical phase, which form a homogenous mixture or a substantially homogenous mixture. In any of the first three cases, a container is filled with the homogenous mixture, where a portion of the mixture used to fill the container contains a mol ratio, mass ratio, and/or volume ratio of the prepared mix. After sealing the container, such as when the temperature of the sealed container is raised, the mix forms a gas mixture at the prepared mixture ratio. The sealed container is then used as a mixed gas container, such as in an anesthetic, a dive tank, for TIG welding, or as a pressure cartridge for preparation of a whipped topping, as described herein. The mix to be packaged is prepared by mixing known amounts of the two or more chemicals, such as by mass, percent, weight, and/or mol ratio where each of the two or more chemicals are present in any amount greater than 0.01, 0.05, 0.1, 1, 2, 5, 10, 25, 30, 40 percent of the mix and less than 99.99, 99.95, 99.9, 99, 95, 90, 75, 70, or 60 percent of the mix. More generally, any 2, 3, 4, 5 or more chemicals are mixed and packaged into the container at the stated percentages. For clarity of presentation and without loss of generality, examples are provided, infra, to further describe the process.

Example I

Still referring to FIG. 11, it is observed that nitrous oxide and molecular oxygen are both in a liquid phase or supercritical phase, which readily mix, in a first set of conditions, comprising temperatures and pressures that are: (1) greater than the melting point of nitrous oxide, −90.86° C.; (2) at pressures greater than the nitrous oxide gas-to-liquid phase change 1152 or the nitrous oxide gas-to-supercritical phase change 1154; and (3) above the molecular oxygen gas-to-supercritical phase change 1164. Said again, in a range of the first set of conditions, nitrous oxide and molecular oxygen mix as the liquid and/or supercritical phases of each of the first chemical, nitrous oxide, and the second chemical, molecular oxygen, mix. Thus, as the mixtures are dominantly homogeneous, in the first set of conditions, a container is readily packaged with mixtures of the nitrous oxide and the molecular oxygen at a ratio of the added components to the mixture.

Example II

Still referring to FIG. 11, it is observed that nitrous oxide and argon are both in a liquid phase or supercritical phase, which readily mix, in a second set of conditions, comprising temperatures and pressures that are: (1) greater than the melting point of nitrous oxide, −90.86° C.; (2) at pressures greater than the nitrous oxide gas-to-liquid phase change 1152 or the nitrous oxide gas-to-supercritical phase change 1154; and (3) above the molecular argon gas-to-supercritical phase change 1174. Said again, in a range of the second set of conditions, nitrous oxide and argon mix as the liquid and/or supercritical phases of each of the first chemical, nitrous oxide, and the second chemical, argon, mix. Thus, as the mixtures are dominantly homogeneous, in the second set of conditions, a container is readily packaged with mixtures of nitrous oxide and argon at a ratio of the added components to the mixture.

Example IV

Still referring to FIG. 11, it is observed that nitrous oxide, molecular oxygen, and argon are all in a liquid phase or supercritical phase, which readily mix, in a third set of conditions, comprising temperatures and pressures that are: (1) greater than the melting point of nitrous oxide, −90.86° C.; (2) at pressures greater than the nitrous oxide gas-to-liquid phase change 1152 or the nitrous oxide gas-to-supercritical phase change 1154; and (3) above the molecular oxygen gas-to-supercritical phase change 1164. Said again, in a range of the third set of conditions, nitrous oxide, molecular oxygen, and argon mix as the liquid and/or supercritical phases of each of the first chemical, nitrous oxide, and the second chemical, molecular oxygen, mix, and the third chemical, argon, mix. Thus, as the mixtures are dominantly homogeneous, in the third set of conditions, a container is readily packaged with mixtures of nitrous oxide, molecular oxygen, and argon at a ratio of the added components to the mixture. More generally, a temperature and/or a range of temperatures and a pressure and/or a range of pressures are selected where each of n chemical are in a phases that spontaneously mix, a mixture or desired proportions of the n chemicals is prepared and packaged/sealed in a container, and the temperature and pressure are transitioned to an operating temperature, such as where all of the chemicals are dispersed as a liquid, as a gas, and/or from a gas headspace, such as at a temperature within 2, 5, 10, or 20° C. of 25° C.

Example V

Still referring to FIG. 11, generally, any two or more chemicals are readily mixed if both chemical are in the same phase, such as both are in a gas phase or both are in a liquid phase, as controlled by temperature and pressure. Further, as liquid and supercritical fluids mix, any two or more chemicals are readily mixed if a first chemical is in a liquid phase and the second chemical is in a supercritical phase, as controlled by temperature and pressure of the mix.

Method of Manufacture

Referring now to FIGS. 12-16, 17(A-B), 18(A-C), and 19(A-C), a method of assembly of a cartridge containing, at a final operating temperature, a mixture, such as a mixture of: gases, liquids, gases and liquids, a gas and a supercritical fluid, and/or a liquid and a supercritical fluid is described. Generally, a process of assembly 1200 includes steps of providing a housing 1210, such as a container 1212, providing a cap/interface 1220, providing a mixture 1230, and after placing the mixture in the housing, sealing the housing and/or sealing the cartridge 1240, such as to form a pressure cartridge 700. Generally, the mixture comprises two or more chemicals in any state or states, such as solid, liquid, gas, or supercritical fluid. For instance, the mixture optionally includes: (1) two or more chemicals in a common phase, such as mixed gas phase at time of manufacture or (2) a first chemical in a first phase and a second chemical in a second phase at time of manufacture. The mixture is then sealed in a container, where the container includes an interface for dispersal of the mixed two or more chemicals. Optionally and preferably, after the step of sealing the cartridge 1240 an additional step of heating the cartridge 1250 is performed, such as bringing the cartridge/canister to room temperature, which results in a phase change of one or more of the contents of the sealed cartridge. For instance, the temperature of the housing is adjusted from a packing temperature to an operating temperature, which optionally and preferably changes the state of one or more chemicals in the mixture, such as from a liquid state into a gas state now contained in the housing and/or contained in the pressure cartridge 700.

Figure 13:
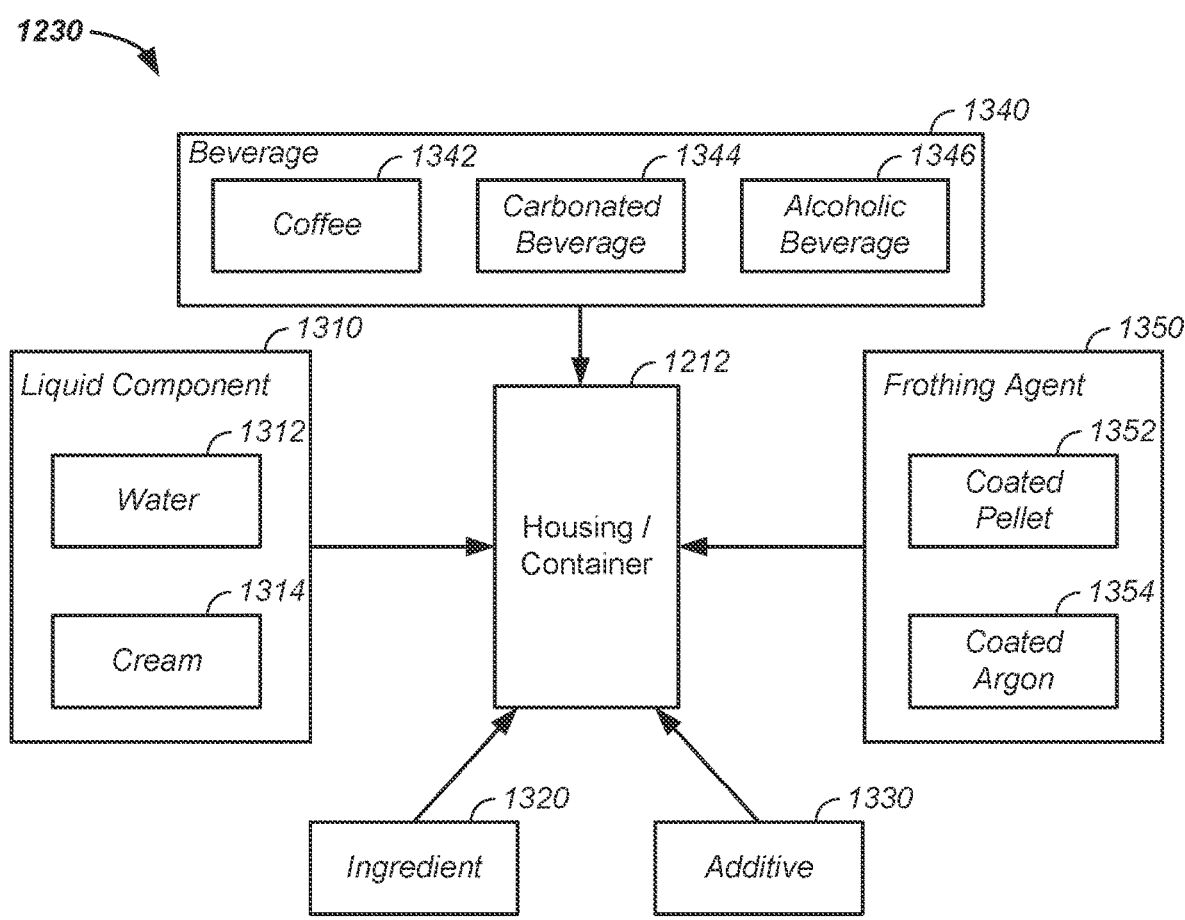
FIG. 13 illustrates a process of filling a container to be sealed.

Referring now to FIG. 13, the process of providing the mixture 1230 to a housing/container in the process of assembling the cartridge 1240/housing/canister/container is further described. Notably, the mixture being placed into the container 1212 before sealing optionally and preferably includes a frothing agent 1350. The frothing agent 1350 is formed by taking a room temperature gas, adjusting pressure and temperature of the gas to form a solid or liquid and then coating the resultant solid or liquid. Subsequent to forming the frothing agent 1350, the frothing agent 1350 is sealed into the cartridge 1240/housing/canister/container. Several examples follow to further describe the process of generating the frothing agent 1350, after an initial description of placing optional additional elements to the container 1212.

Still referring to FIG. 13, the process of providing the mixture 1230 to a housing/container in the process of assembling the cartridge 1240/housing/canister/container is further described. Optionally and preferably, a liquid component 1310 of a beverage is added to the container 1212, such as water 1312 or cream 1314. Optionally, an ingredient 1320 is added to the container 1212, such as a sweetener, a chemical, a natural product, an organic acid, a fatty acid, a starch, a gum, and/or a salt. Optionally, an additive 1330 is added to the container 1212, such as a preservative, a sweetener, a flavoring, and/or a coloring. Indeed, an entire beverage 1340 is optionally added to the container 1212, such as a coffee 1342, a tea, a carbonated beverage 1344, a juice, and/or an alcoholic beverage 1346. With or without adding one or more of the liquid component 1310, the ingredient 1320, the additive 1330, and the beverage 1340 to the container 1212, the frothing agent 1350 is optionally and preferably added to the container 1212. The frothing agent 1350 is further described infra.

Frothing Agent

Figure 14:
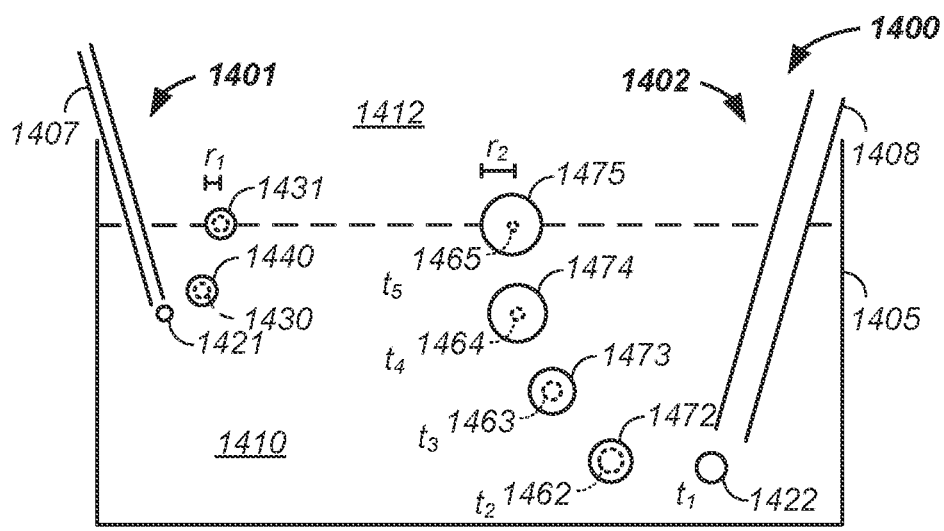
FIG. 14 illustrates a first process of coating a room temperature gas when in solid or liquid form.
Figure 15:
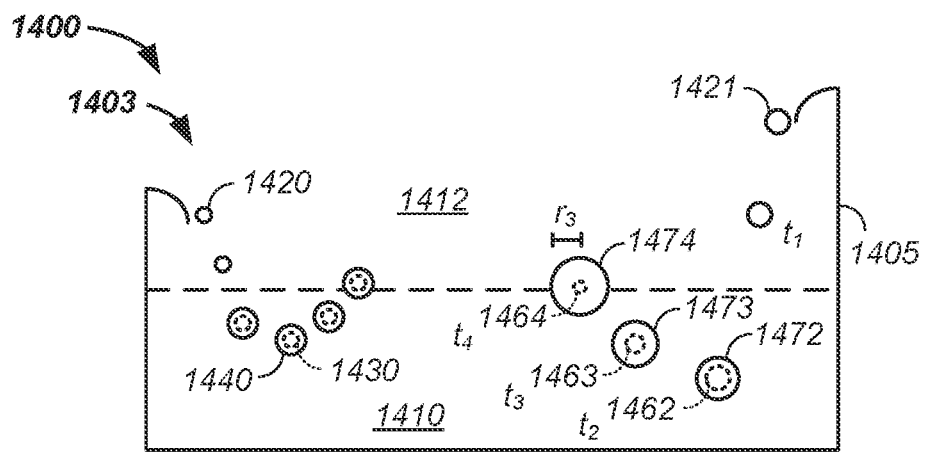
FIG. 15 illustrates a second process of coating a room temperature gas when in solid or liquid form.
Figure 16:
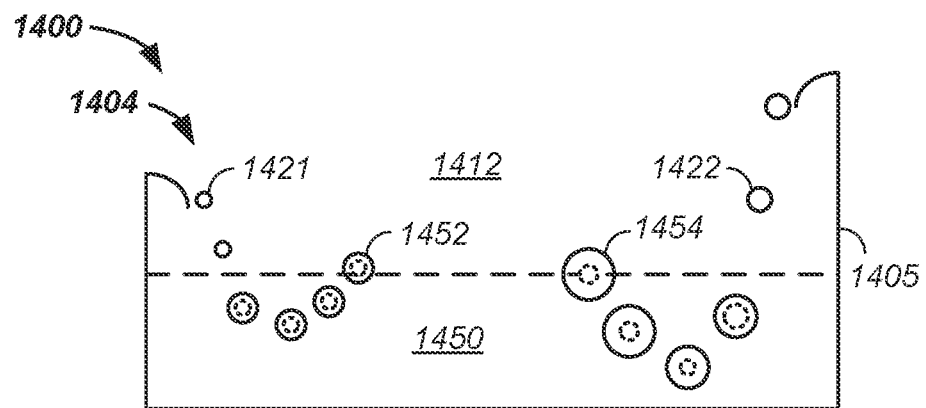
FIG. 16 illustrates a process of forming cream particles.

Referring still to FIG. 13 and referring now to FIGS. 14-16, the frothing agent 1350 includes a chemical that is in a gas phase at room temperature and pressure, but at time of packaging is packaged at a temperature or pressure resultant in the chemical being in a solid, liquid, or supercritical fluid state where the solid or liquid state is at least partially contained in a coating at an instant of manufacturing. More particularly, the solid, such as a pellet, or liquid, such as a drop, is at least 50, 60, 70, 80, 90, 95, or 99% contained within the coating immediately after, such as in less than 1, 5, 10, 50, or 100 seconds, when the solid or pellet initially makes contact with a second liquid, such as an aqueous solution or a fat solution.

For clarity of presentation and without loss of generality, a coated form of nitrous oxide is used as an illustrative example of the frothing agent 1350, where the nitrous oxide is optionally any other chemical or mixture of chemicals that is a gas or a mixture of gases at room temperature, respectively. Several non-limiting examples are provided to further describe the frothing agent 1350.

Example I

Still referring to FIG. 13, a first example of forming/packing/applying a frothing agent 1350 is provided. In this example, nitrous oxide is the chemical that is a gas at room temperature and pressure. The nitrous oxide, is compressed and/or is cooled to form a solid or liquid, such as at temperatures and pressures illustrated in FIG. 11. The solid or liquid form of nitrous oxide is coated with a coating, such as with ice, a water based coating, a lipid, and/or a lipid based coating. For instance, a pellet of the nitrous oxide is placed in water. An ice layer forms about the nitrous oxide to form a coated pellet 1352. Similarly, if argon, as a solid or as a liquid, is placed into water, then a coated argon 1354 form of a coated pellet 1352 is formed. More generally, any solid form, liquid form, or supercritical fluid form of a room temperature and pressure gas or mixture of gases is coated, such as with an ice layer, to form a coated pellet 1352. Optionally, any solid form, liquid form, or supercritical fluid form of a room temperature and pressure gas or mixture of gases is coated, such as with an lipid layer, to form a coated pellet 1352. That is the coating material is optionally any homogenous or inhomogeneous layer or set of two or more layers where each layer is of any thickness, such as less than 10, 5, 2, 1, 0.5, 0.2. 0.1, 0.05, 0.01, or 0.001 mm thick. After placing the frothing agent 1350 into the container 1212, along with an optional component, such as illustrated in FIG. 13, the container 1212 is sealed. After an optional time period where the contents of the sealed container are warmed by greater than 5, 10, 20, 50, or 100° C. from a packing temperature, the sealed container is opened, such as to an ambient environment and/or such as through a delivery port 1740, further described supra. Upon exposure to a lower pressure environment, the frothing agent 1350, melts and/or expands such as in the presence of a lipid to form a froth, foam, or whipped cream. In a first case, the item being frothed, such as a lipid or cream, is packaged with the frothing agent 1350, such as in the form of the coated pellet 1352, in the container 1212. In a second case, the item being frothed, such as a lipid or cream, is packaged in a system replaceably attached to the container 1212, such as a secondary container and/or the profi 600, via the delivery port 1740, where the cream is immediately frothed in the secondary container and/or is frothed upon opening the secondary container to a standard atmospheric pressure.

Example II

Referring now to FIG. 14, a second example of forming coated pellets 1352, is provided. In this example, a method of bubbling 1400 the pellet core 1430 through a liquid 1410, such as water to form the coated particle 1352, is illustrated, which optionally results in controlled and varying sizes of coated pellets.

Still referring to FIG. 14, a first bubbling system 1401, is illustrated. Generally, a tube, such as a first tube is provided through which a core material, such as nitrous oxide in a solid or liquid form, is injected into the liquid 1410 held in a container 1405. A pellet or drop of the frozen, liquid, cold, and/or low temperature core material, such as nitrous oxide in a solid or a liquid phase, freezes and/or causes a phase change of a portion of the liquid 1410 into a solid form, coating layer, and/or coating 1440 about the pellet core 1430 or any remaining portion of the pellet core 1430 to form a first coated pellet 1431. As illustrated, a first particle/pellet/drop size 1421 of the core material 1430, is injected into the liquid, such as through a first deliver port/tube 1407 with a first port diameter. When the first particle size 1421 of the core material 1430 freezes a portion of the liquid 1410, a first coating layer 1440 forms around the core material 1430 to form the first coated pellet 1431, which is an example of the coated pellet 1352. In the case of the first drop size 1421 of the core material 1430, the first coated pellet 1431 forms with a first radius, $r_1$, or first mean particle size.

Still referring to FIG. 14, a second bubbling system 1402, is illustrated. As in the first bubbling system 1401, the core material 1430 is injected into the liquid 1410. As illustrated, a second particle/pellet/drop size 1422 of the core material 1430, is injected into the liquid 1410, such as through a second delivery port/tube 1408 with a second diameter. When the second drop size 1422 of the core material 1430 freezes a portion of the liquid 1410, a second coated pellet 1432 forms with a second radius, $r_2$, or second mean particle size. Generally, a thickness of the coating 1440 of the coated particle 1352 is optionally and preferably controlled by controlling the size, diameter, volume, and/or mass of the solid or liquid pellet placed into the liquid 1410.

Still referring to FIG. 14, the second bubbling system 1402 is further described. As illustrated, the core material 1430 has an initial size at a first time, $t_1$, and respectively reduced sizes 1462, 1463, 1464, and 1465 at a second, third, fourth, and fifth time while the thickness of the coating has respectively increased sizes 1472, 1473, 1474, and 1475 at the second, third, fourth, and fifth times, which is a result of heat traveling from the liquid 1410 into the core material 1430, which forms a thicker coating while phase changing the solid or liquid core into a liquid or gas, respectively. Generally, the size of the coated pellet 1352 is optionally and preferably controlled by the size of the particle/pellet/drop of the core material 1430 added to the liquid 1410 and/or the amount of time the core material 1430 is exposed to the liquid 1410. Similarly, the ratio of the mass of the core material-to-the mass of the coating layer 1440 is controlled by the size of the particle/pellet/drop of the core material 1430 added to the liquid 1410 and/or the amount of time the core material 1430 is exposed to the liquid 1410.

Referring now to FIG. 15, a dropping system 1403 is described to form coated pellets 1352. Generally, the dropping system 1403 follows the same principles as the first and second bubbling systems 1401, 1402; however, the pellet/liquid, such as $N_2O_{(s)}$ or $N_2O_{(l)}$, is dropped into the liquid 1410 rather than being injected into and bubbled through the liquid 1410. The dropping system 1403 still results in the core material 1430 being coated with the coating 1440, adsorbing onto the coating and/or absorbing into the coating 1440 to form the coated pellet 1352, which is also referred to herein as a frothing loaded particle, such as when the nitrous oxide is absorbed into the coating 1440. As illustrated, one or more particle/drop sizes 1420, such as the first drop size 1421, the second drop size 1422, and a third drop size 1423 are dropped into the liquid 1410 to form coated pellets 1352 of varying dimensions. As illustrated, a third coated pellet 1433 forms with a third radius, $r_3$, or third mean particle size.

Referring again to FIG. 14 and still referring to FIG. 15, during manufacturing, the coated pellets 1352 are optionally skimmed from the top of the liquid 1410, such as where the nitrous oxide coated pellet has a lower density than the liquid.

Still referring to FIG. 15, generally, any number of sizes of coated pellets are formed, such as with particles in any range from less than 1, 0.5, 0.1, 0.05, 0.01, and 0.001 mm mean cross-section length to any range greater than 0.01, 0.05, 0.1, 0.5, 1, and 2 mm mean diameter. A range of sizes of the coated pellets 1352 is beneficial when being added to another component, such as cream, as the range of sizes of the coated particles will cool the cream at various rates, which reduces likelihood of locally freezing the cream.

Referring now to FIG. 16, a fourth system 1404 is described for forming coated pellets 1352 and/or pellets with the core material, such as $N_2O_{(s)}$ or $N_2O_{(l)}$, at least partially or totally absorbed into the coating 1440, such as in the form of $N_2O_{(g)}$. In the fourth system 1401, the particle or droplet 1420 is coated with a hydrophilic substance 1450, such as a cream, a fatty acid, and/or a lipid. As illustrated, a first smaller lipid coated pellet 1452 is formed from a first smaller pellet, 1421, such as a nitrous oxide solid pellet, and a second larger lipid coated pellet 1454 is formed from a second larger pellet/drop 1422, such as a nitrous oxide liquid drop. In this manner, the formed coated pellet 1352 is a cream with a nitrous oxide core at time of manufacturing, where the nitrous oxide core is optionally at least partially and/or totally absorbed into the cream, such as in a gas phase in the hydrophobic liquid. In this manner, a particle is formed, which is optionally packaged into a container, such as a whipped cream canister.

Referring again to FIGS. 14-16, the particles/drops 1420 are optionally any mixture of solids and/or any mixture of liquids, such as mixtures of nitrous oxide and argon, mixtures of nitrous oxide and nitrogen, or mixtures of nitrous oxide, argon, and nitrogen.

Optionally, all of the solid/liquid form of the nitrous oxide undergoes a phase change in the coating process, in which case at least a portion, such as greater than 1, 2, 5, 10, 25, 50, or 75% of the nitrous oxide is dissolved/captured in the coated pellet, where the coated pellet comprises the coating 1440 embedded with any remaining portion of the first pellet core material. For clarity of presentation, herein the coated pellet 1431 refers to a pellet having a core and a coating and/or refers to the coating material with embedded core coating material. Optionally and preferably, in the manufacturing process the resultant coated pellet: (1) sinks, where it is scraped in a collection step; (2) floats where it is skimmed in a collection step, or (3) is suspended, where it is strained in a collection step.

Still referring to FIGS. 14-16, the coated pellet 1352 is optionally coated with an additional n layers, such as to form a second, third, fourth, or greater layer. For instance, the coated pellet 1352, is optionally brought down to a temperature and/or increased in pressure, such as to maintain/bring the nitrous oxide core to a solid or liquid phase. The coated pellet 1352 is brought into contact with another liquid to form a second coating and the process is optionally repeated to form additional layers.

Cartridge Formation/Sealing

For clarity of presentation and without loss of generality, several examples of forming the cartridge and/or sealing the cartridge are provided.

Example I

In a first example, a cartridge, such as the pressure cartridge 700, is formed by rolling or forming a housing material, such as sheet steel, into a base shape, such as a test tube shape, cylinder shape, or container shape; the base shape, such as the test tube shape, is sealed at the bottom, such as the sheet steel is heated and crimped to form a sealed bottom; a neck is formed from the base shape, such as the sheet steel is heated and/or deformed into a neck, which is ready to fill; an assembly bit surrounds the neck; the mixture and/or chemicals are inserted into the cartridge/container, such as through the assembly bit; and/or a capping mechanism seals a cap to the neck with the two or more chemicals inside the now sealed container, where the pressure and temperature of the inserted chemicals are at temperatures and pressures illustrated in FIG. 11.

For clarity of presentation and without loss of generality, several additional examples are provided of methods for sealing the cap to the base shape.

Example II

In a second example, the cap is sealed to the neck of the base shape by crimping the cap.

Example III

Figure 17A:
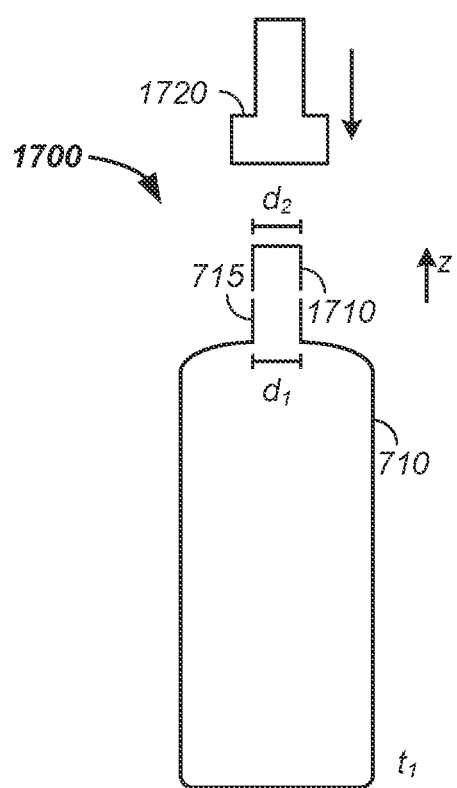
FIG. 17A and FIG. 17B illustrate a galling capping step and an assembled cartridge step, respectively.
Figure 17B:
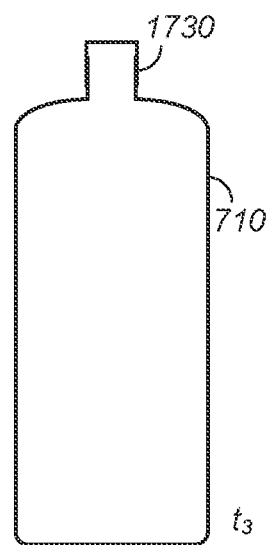

In a third example, referring now to FIG. 17A and FIG. 17B, a friction sealing process 1700 of sealing a cap 1710 to a receiving element 715, such as a neck of the outer pressure wall 710 of the pressure cartridge 700/base shape is described. Generally, the receiving element 715, such as a neck, has a first diameter, $d_1$, such as an outer diameter, and the cap 1710 has a second diameter, $d_2$, such as an inner diameter, or vice versa, where the first and second diameters are closely matched. A pressing element 1720 presses the cap 1710 onto the receiving element 715. The first and second diameters are matched closely enough that galling occurs, where one surface essentially fuses to the other. For instance, during the pressing process or a similar tightening process of matched threads, friction pressure builds, which heats/deforms the parts and/or breaks down a coating, such as an oxide coating, of the parts. As a result, the surface of the sealing cap and the surface of the receiving element are exposed to one another and fuse together and/or seize, which forms a friction seal 1730 of the pressure cartridge 700. Generally, the mixture of at least a first and second chemical is placed into the pressure cartridge prior to the step of sealing the container. Optionally and preferably the cap 1710 includes an interface, such as a delivery port 1740, to a regulator or auxiliary device, such as the profi 600, a TIG welder system, an anesthesiology system, or diving equipment.

Example IV

Figure 18A:
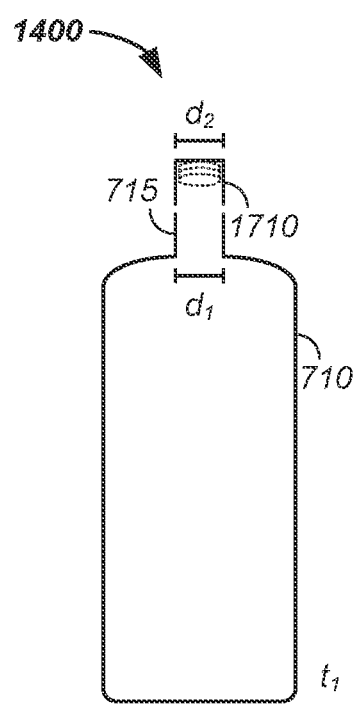
FIG. 18A, FIG. 18B, and FIG. 18C illustrate initial, intermediate, and final cold welding steps, respectively.
Figure 18B:
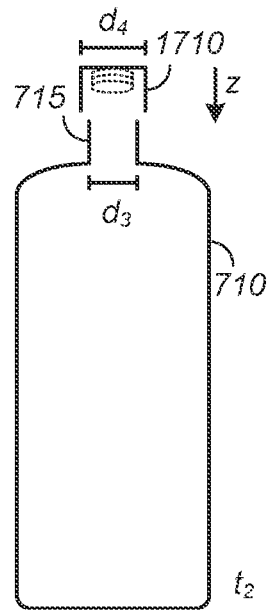
Figure 18C:
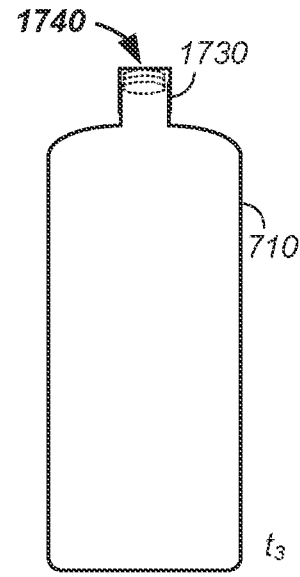

In a fourth example, referring now to FIG. 18A, FIG. 18B, and FIG. 18C, a cold welding sealing process 1800 of sealing the cap 1710 to the receiving element 715, such as a neck of the outer pressure wall 710 of the pressure cartridge 700/base shape is described. Generally, the receiving element 715, such as a neck, has a first diameter, $d_1$, such as an outer diameter, and the cap 1710 has a second diameter, $d_2$, such as an inner diameter, or vice versa, where the first and second diameters are closely matched or are the same at a common temperature and/or at a first temperature of the cap 1710 and second temperature of the receiving element 715 within 25° C. of each other. Referring now to FIG. 18B, as illustrated the cap 1710 and the receiving element 715 are at different temperatures, such as differing by greater than 25° C. In a first case, the cap 1710 is heated to and/or is maintained at a temperature greater than 5, 10, 20, 25, 50, or 100° C. greater than the receiving element 715. As the mixture of two or more chemicals are optionally and preferably delivered to an inner volume within the outer pressure wall 710 as a solid, liquid, or supercritical fluid, the receiving element 715 is optionally and preferably maintained at a low temperature, such a less than 25, 20, 15, 10, 0, −25, −50, −100, or −150° C. In the situation of the cap 1710 being a different temperature than the receiving element 715, the size of the cap 1710 and the size of the receiving element are different. Referring now to FIG. 18B, a case is illustrated where the inner diameter, $d_4$, of the higher temperature cap 1710 has expanded to be greater than the outer diameter, $d_3$, of the lower temperature receiving element 1715. The cap 1710 is placed around the receiving element 715, with or without use of the galling process of the preceding example, and then the receiving element 715 and the cap 1710 are brought to the same temperature, where upon the third diameter, $d_3$, and the fourth diameter, $d_4$, converge to a common diameter and a cold weld seal 1730 between the cap 1710 and the receiving element 715 is formed. More generally, the cap 1710 is optionally heated, held at a room temperature or cooled while the receiving element 715 is optionally heated or cooled until the cap 1710 and receiving element 715 are joined or vice versa. The key is that the mating elements are brought together at initially different temperatures and then allowed to come to a common temperature to form the cold weld seal 1730. Optionally and preferably, the cap 715 and the receiving element 715 are constructed of the same material, but different materials are optionally used.

Example V

Figure 19A:
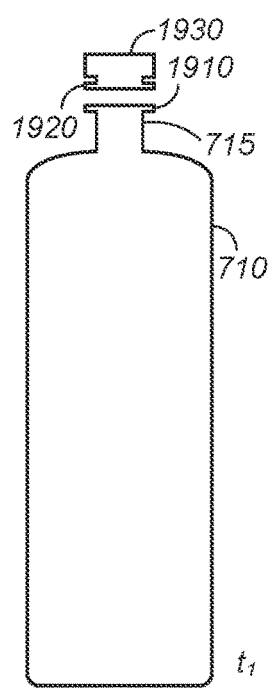
FIG. 19A, FIG. 19B, and FIG. 19C illustrate initial, intermediate, and final cold flange sealing steps, respectively.
Figure 19B:
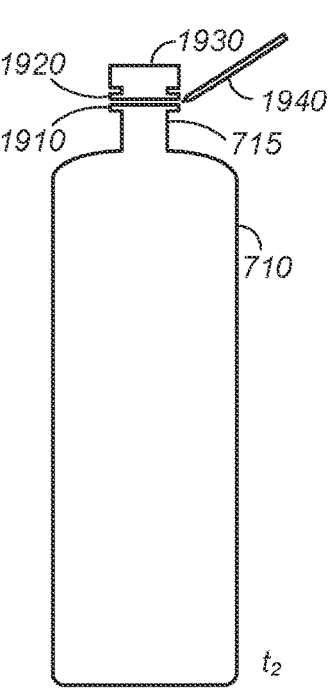
Figure 19C:
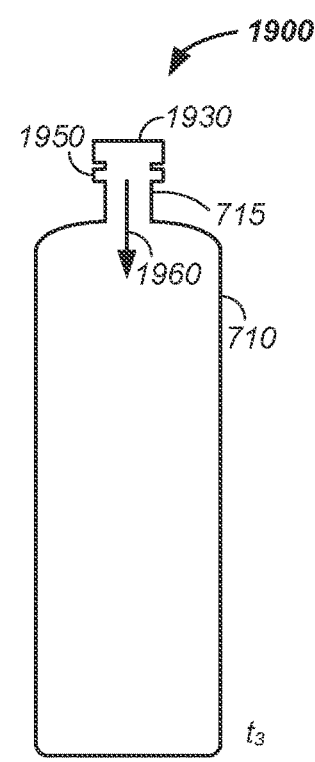

In a fifth example, referring now to FIG. 19A, FIG. 19B, and FIG. 19C, a flange sealing process 1900 is illustrated. Generally, after 1, 2, 3, or more components of the mixture are placed into a volume peripherally contained by the outer pressure wall 710, a cap is sealed to the outer pressure wall. Referring still to FIG. 19A, the receiving element 715 is configured with a first flange 1910, radially projecting rim, and/or radially extending flat rim and a flanged cap 1930, which is a species of the cap 1710, has a second flange 1920, which also extends radially outward from a central axis of the flanged cap 1910. At a first time, $t_1$, the second flange 1920 of the flanged cap 1930 and the first flange 1910 of the receiving element 715 are brought together and at a second time, $t_2$, a welder 1940 is used to join the first flange 1910 and the second flange 1920, such as by welding a radially outward perimeter of the physically positioned and joined flanges 1910, 1920, which results in a welded flange 1910 joining the flanged cap 1930 and/or the cap 1710 to the flanged neck, neck 715, or outer housing 710 to form a welded seal 1950 of the pressurized cartridge 700 or container at the third time, $t_3$. As illustrated by heat flow 1960, the small mass of the first flange 1910 and second flange 1920 results in low heat flow into the body of the pressure cartridge 700, which allows formation of the welded seal 1950 while maintaining contents of the pressure cartridge at chilled temperatures, such as less than 25, 0, −50, or −100° C.

Optionally, one or more of the chemicals in the mixture added into and sealed into the pressure cartridge 700 is initially in a solid form. In this case, the solid form of one or more of the chemicals of the mixture in solid form is cut/weighed and the solid is dropped into/positioned in the container, where zero, one, or more chemicals in a gas, liquid, and/or supercritical phase are added to the solid in the container prior to sealing.

The amount of each of the two or more chemicals placed into the container prior to sealing is measured, such as by mass, percent, mole ratio, partial pressure, volume, ratio, density, and/or fraction. For example, if adding a solid component of the mixture, optionally and preferably a mass of the solid component is added. For instance, if the density and purity of the solid component is known, a predefined cutter shape is optionally and preferably used to cut out and drop into the container a known mass of the solid component. Similarly, if the density and purity of a liquid or a supercritical fluid component is known, then a volume or a mass of the liquid is optionally delivered into the container. Similarly, if a density/pressure of a gas component is known, then a volume, delivery time from a pressurized container, and/or a total gas flow volume is used to deliver the gas component to the container. Similar processes are optionally used to deliver mixes of solids, liquids, gases, supercritical fluids, or liquid-supercritical fluid combinations. More generally, relative amounts of different components of the mixture, such as measured by mass, volume, density, and/or moles, are added to the pressure cartridge 700 or container prior to sealing.

For clarity of presentation and without loss of generality, two examples of a nitrous oxide containing pressure cartridge is provided, where the nitrous oxide containing pressure cartridge is used to charge the profi 600.

Example I

In a first example, the nitrous oxide is packaged into the pressurized cartridge 700 with argon gas. If the ratio of the nitrous oxide to the argon gas is preferably 30:70 by volume or mass, then a mixture of the nitrous oxide and argon is optionally prepared in or transformed into any state. For instance, referring again to FIG. 11, at 0° C. and 60 bar, both the nitrous oxide and the argon are in a supercritical phase. If the supercritical phase mixture is prepared with the 30:70 ratio of nitrous oxide-to-argon, then a volume and/or a mass of the supercritical fluid is optionally placed into a volume circumferentially enclosed by the outer pressure wall 710 or container prior to capping and formation of the now filled pressurized cartridge 700. When the, now sealed, nitrous oxide and argon filled pressurized cartridge is brought to room temperature, such as 25° C., the nitrous oxide-argon mix in the pressurized cartridge 700, dependent upon the total volume of the added supercritical mixture and the total volume of the pressurized cartridge, will: (1) stay in a supercritical phase at sufficient pressure; (2) form a nitrous oxide headspace above the supercritical argon fluid; or (3) most preferably form a nitrous oxide-argon gas mixture, such as at pressures below the argon gas-to-supercritical fluid interface 1174 and/or the nitrous oxide gas-to-liquid interface 1152, while maintaining the desired percent nitrous oxide and the desired percent argon. Similarly, referring still to FIG. 11, if the temperature and pressure of the initial mixture of nitrous oxide and argon maintained the nitrous oxide and the argon in a liquid phase, such as at −150° C. and 25 bar and a mass or volume of the liquid mix (or individual masses or each component) is added to the pressurized container before sealing, then, after sealing and bringing the container to room temperature, 25° C., the nitrous oxide and the argon will transition into a gas phase mixture having crossed their respective gas-to-liquid phase change interfaces 1152, 1172, and the resultant mixture has the desired nitrous oxide gas-to argon gas ratio of as packaged mixture, albeit now at a user operable temperature and pressure. Nitrogen or molecular nitrogen is optionally used in place of some or all of the argon in this example. More generally, any individual or two or more components of the mixture packaged into a pressurized container, such as the pressurized cartridge 700, are optionally in a solid, liquid, or supercritical fluid phase at a set volume and/or mass in the pressurized container prior to capping, where after transitioning the container to an operating temperature, such as within 0, 1, 2, 5, 10, 15, 25, 50, or 75° C. of a room temperature of 25° C., the container contains the desired mix of gases.

Example II

In a second example, a profi charging pressurized cartridge is described, where the pressurized cartridge is charged with an eight gram mixture, the eight grams including four grams of nitrous oxide and four grams of argon. Eight grams is used as expansion of the eight grams of compressed gas charges or recharges a standard one liter profi or whipped cream cartridge. Instead of packing the pressurized cartridge by mass, equivalent manners of packing the cartridge with the same 50:50 mixture of nitrous oxide-to-argon by mass include packing the cartridge with any of: (1) a mixture of 44 g or nitrous oxide-to 40 grams of argon; (2) 0.091 moles of nitrous oxide-to 0.100 moles of argon; (3) a 0.476:0.524 mole ratio of nitrous oxide-to-argon; (4) 3.28 mL of nitrous oxide to 2.87 mL of argon; or (5) 3.28 grams of solid nitrous oxide to 2.42 grams of solid argon. Stated again, the cartridge or pressurize cartridge 700 is optionally packaged with solids, liquids, and/or supercritical fluids that phase change to the desired mixture of gases at operating temperatures. Similarly ratios of nitrous oxide-to-molecular nitrogen are calculated as are ratios of three or more chemicals in the mixture. Adjustments are optionally and preferably made for losses in the packing process, such as due to phase changes from heating prior to sealing.

Generally, the cap 1710 includes a delivery port that couples to a receiving port of a desired system or apparatus.

For example, the cap 1710 optionally and preferably includes the delivery port 1740 that couples to the receiving port 630 of the profi 600, which allows charging the profi 600 with the desired mixture of gases in the pressurized cartridge 700. Optionally, the delivery port is integrated into any part of the pressurized cartridge 700.

Once sealed, the pressure container and/or contents therein, are brought from a manufacturing temperature and pressure, such as any temperature and pressure illustrated in FIG. 11, to a shipping/use temperature and pressure, where a difference in the manufacturing temperature and use temperature is zero degrees or greater than 10, 20, 30, 40, 50, 60, 70, 80, 90, or 100° C. and a difference in the manufacturing pressure and a pressure at the time of delivery of the mixed chemicals from the container is zero bar or greater than 5, 10, 20, 30, 40, 50, or 60 bar, where an optional and preferred operating/use temperature and pressure is an atmospheric pressure±less than 5, 10, 15, 20, 30, 40, 50, 100, 200, and 500 percent and within 1, 5, 10, 20, and 25° C. of 25° C.

An additional example of packaging a dispensable substance with the techniques described herein is provided. In this example a method for packaging a dispensable substance is described, such as a method for packaging a food product, such as whipped cream, a soda or beverage, and/or a non-food product, such as a lubricant or an air freshener. More generally, the example illustrates packaging any product in a pressurized container, such as a hand-held spray can weighing less than ten pounds, or a pressurizing container, such as a floor mounted user portable container weighing less than one hundred pounds. The method of manufacture comprises the steps of: (1) placing a first product component into a container, where the container includes a valve dispensing port, such as a spray nozzle or pressurizing connection to pressurize a secondary container such as a profi; (2) adding a second product component into the container, such as nitrous oxide, argon, carbon dioxide, and/or an air component where the air component is at a concentration at least twice that found in our standard atmosphere on Earth, where the second product component comprises at least one of: (a) a solid form of the second product component and (b) a liquid form of the second product component; (3) sealing the container; and (4) warming, after the step of sealing, the second product component in the container at least ten degrees Celsius, where the step of warming results in a phase change of the second product component into a gas phase, at least a portion of the gas phase of the second product component dissolving into the first product component to form the dispensable substance. Optionally and preferably, a gas phase of the second product is used to propel the dispensable substance from the container, such as after a phase change of the second product to a final pressure at least 0.5, 0.26, 0.25, or 0.1 atm greater than an initial pressure in the container of less than 2, 1.5, 1.31, or 1.1 atm. For instance, a hydrocarbon lubricant or and air freshener is optionally and preferably dispensed by the second product, where the second product is at least fifty percent carbon dioxide; the second product infuses a beverage, such as a soda; or a whipped cream is dispensed from the container with a gas mixture as described supra. Optionally and preferably, the container is pre-chilled, such as to a temperature of less than 15, 10, 0, −10, or −20 Celsius, such as before adding at least one of the first and second product components to the container. Generally, the process of the second product pervading the first product minimizes and/or completely eliminates the use of very expensive gasser-shakers in industry, which typically exceed one million dollars each in production lines.

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to optionally be modified by the term "about", whether or not the term is explicitly used, unless explicitly stated otherwise. As used herein, the singular forms "a," "an," and "the" include plural referents unless the context clearly dictates otherwise.

The clause "atmospheric pressure" as used herein refers to ambient pressure of about 1 atmosphere (atm), or about 1 bar at sea level.

The clause "room temperature" as used herein is about 25° C.

All percentages (%) are by weight unless indicated otherwise in a specific circumstance.

Optionally, any element of the container, such as a body of the container is printed using three-dimensional metal printing technology, such as in an additive manufacturing process.

Herein, a set of fixed numbers, such as 1, 2, 3, 4, 5, 10, or 20 optionally means at least any number in the set of fixed number and/or less than any number in the set of fixed numbers.

In still yet another embodiment, the invention comprises any combination and/or permutation of any of the elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. While single PWM frequency, single voltage, single power modules, in differing orientations and configurations have been discussed, adaptations and multiple frequencies, voltages, and modules may be implemented in accordance with various aspects of the present invention. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for packaging a dispensable substance, comprising the steps of:
   placing a first product component into a container, said container comprising a valve dispensing port;
   adding a second product component into said container, said second product component comprising at least one of: (1) a solid form of said second product component and (2) a liquid form of said second product component;
   sealing said container;
   warming, after said step of sealing, said second product component in said container at least ten degrees Celsius, wherein said step of warming results in a phase change of all of said second product component into a gas phase, at least a portion of said gas phase of said second product component dissolving into the first product component to form the dispensable substance; and
   propelling the dispensable substance from said container with the gas phase of said second product.

2. The method of claim 1, further comprising the step of:
   increasing pressure in said container, through the phase change of the second product, to a final pressure at least 0.26 atm greater than an initial pressure in the container of less than 1.31 atm.

3. The method of claim 2, further comprising the step of:
   propelling the first product from said container with the second product, wherein the first product comprises at least one of a hydrocarbon based solvent and an air freshener, wherein the second product comprises at least fifty percent carbon dioxide.

4. The method of claim 2, further comprising the step of:
   prior to said step of adding, pre-chilling said container to a temperature of less than five degrees Celsius.

5. The method of claim 4, further comprising the steps of:
   dispensing from container, at a pressure exceeding two hundred pounds per square inch, a mixture comprising:
   greater than twenty percent by mass nitrous oxide; and
   at least three percent by mass of at least one of molecular hydrogen, helium, molecular nitrogen, carbon dioxide, neon, argon, krypton, and xenon.

6. The method of claim 1, further comprising the step of:
   increasing pressure in said container, through a phase change of the second product, to a final pressure at least 0.25 atm greater than an initial pressure in the container of less than 1.3 atm.

7. The method of claim 6, said step of adding the second product further comprising at least one of the steps of:
   putting at least one gram of carbon dioxide into a beverage; and
   putting at least one-fiftieth of a gram of nitrous oxide into the beverage.

8. The method of claim 1, further comprising the step of:
   prior to said step of adding, pre-chilling said container to a temperature of less than ten degrees Celsius.

9. The method of claim 1, further comprising the steps of:
   dispensing from said container, at a pressure exceeding two hundred pounds per square inch, a mixture comprising:
   greater than thirty percent by mass nitrous oxide; and
   at least three percent by mass of at least one of molecular hydrogen, helium, molecular nitrogen, carbon dioxide, neon, argon, krypton, and xenon.

10. The method of claim 9, said step of dispensing further comprising the step of:
    pressurizing a secondary container containing cream.

11. The method of claim 1, further comprising the step of:
    permeating the first product with the second product in said container, the first product comprising at least one of a cream, a fat, and a butterfat, wherein the second product comprises at least thirty percent nitrous oxide.

12. The method of claim 11, further comprising the step of:
    coating at least forty percent of a surface area of said second product in ice prior to said step of adding.

13. The method of claim 1, further comprising the steps of:
    forming a beverage with the first product and the second product; and
    at least one of the steps of:
    putting at least one of gram carbon dioxide into the beverage; and
    putting at least one-tenth of a gram of nitrous oxide into the beverage.

14. The method of claim 1, further comprising the step of:
    coating at least fifty percent of a surface area of said second product in ice prior to said step of adding.

15. The method of claim 1, said step of placing comprising the step of putting argon into said container.

16. The method of claim 1, further comprising the step of:
    forming a pressurized cartridge containing argon and nitrous oxide, said step of placing comprising the step of putting argon into said container.

17. The method of claim 16, further comprising the step of:
    pressurizing a profi container with said pressurized cartridge.

* * * * *